United States Patent
Tuschel et al.

(10) Patent No.: US 7,471,389 B2
(45) Date of Patent: Dec. 30, 2008

(54) SYSTEM AND METHOD FOR FIBER ARRAY SPECTRAL TRANSLATOR BASED POLYMORPH SCREENING

(75) Inventors: David Tuschel, Monroeville, PA (US); Patrick J. Treado, Pittsburgh, PA (US); Matthew P. Nelson, Harrison City, PA (US)

(73) Assignee: ChemImage Corporation, Pittsburgh, PA (US)

( * ) Notice: Subject to any disclaimer, the term of this patent is extended or adjusted under 35 U.S.C. 154(b) by 133 days.

(21) Appl. No.: 11/682,302

(22) Filed: Mar. 5, 2007

(65) Prior Publication Data

US 2007/0206185 A1 Sep. 6, 2007

Related U.S. Application Data

(60) Provisional application No. 60/778,794, filed on Mar. 3, 2006.

(51) Int. Cl.
*G01J 3/44* (2006.01)
*G01N 21/65* (2006.01)

(52) U.S. Cl. ...................... 356/301; 356/328
(58) Field of Classification Search ................ 356/300, 356/301, 328
See application file for complete search history.

(56) References Cited

U.S. PATENT DOCUMENTS

| | | | |
|---|---|---|---|
| 4,781,458 A | 11/1988 | Angel et al. | |
| 5,534,997 A | 7/1996 | Schrader | |
| 5,615,673 A | 4/1997 | Berger et al. | |
| 5,963,319 A | 10/1999 | Jarvis et al. | |
| 6,100,975 A | 8/2000 | Smith et al. | |
| 6,483,581 B1 | 11/2002 | Ben-Amotz et al. | |
| 6,486,948 B1 | 11/2002 | Zeng | |
| 6,867,858 B2 | 3/2005 | Owen et al. | |
| 7,072,770 B1 | 7/2006 | Schweitzer et al. | |
| 2002/0048610 A1 | 4/2002 | Cima et al. | |
| 2003/0059837 A1 | 3/2003 | Levinson et al. | |
| 2003/0162226 A1 | 8/2003 | Cima et al. | |
| 2005/0089923 A9 | 4/2005 | Levinson et al. | |
| 2005/0095696 A9 | 5/2005 | Lemmo et al. | |
| 2005/0191614 A1 | 9/2005 | Cima et al. | |
| 2006/0124443 A1* | 6/2006 | Tuschel et al. | 204/157.92 |
| 2008/0151225 A1* | 6/2008 | Treado et al. | 356/73 |

OTHER PUBLICATIONS

Manolakis, D. et al., "Hyperspectral Subpixel Target Detection Using the Linear Mixing Model," IEEE Trans. on Geoscience and Remote Sensing, Jul. 2001, V. 39, No. 7, pp. 1392-1409.

Anquetil, P., et al. "Laser Raman Spectroscopic Analysis of Polymorphic Forms in Microliter Fluid Volumes," J. of Pharma. Sciences, Jan. 2003, V. 92, No. 1, pp. 149-161.

(Continued)

*Primary Examiner*—F. L Evans
(74) *Attorney, Agent, or Firm*—Duane Morris LLP

(57) ABSTRACT

The present disclosure describes methods and systems that combine Raman spectroscopy performed in a manner that utilizes one or more of widefield illumination, simultaneous multipoint Raman spectral acquisition, and spectral unmixing for the purpose of high throughput polymorph screening. Features of this methodology include: (a) high throughput polymorph screening to reduce crystal orientation effects on Raman spectra; (b) in-well multi-polymorph screening using increased statistical sampling; and (c) multipoint spectral sampling to enable spectral unmixing.

73 Claims, 14 Drawing Sheets

OTHER PUBLICATIONS

Carter, J.C., et al., Multi-Wavelength Raman Imaging Using a Small-Diameter Image Guide with a Dimension-Reduction Imaging Array, Appl. Spectro, 2003, V57, No. 7, pp. 761-767.

Ma, Jiaying and Ben-Amotz, Dor, "Rapid Micro-Raman Imaging Using Fiber-Bundle Image Compression," Applied Spectroscopy; 1997, V. 51, No. 12, pp. 1845-1849.

Nelson, M. et al., Single-Frame Chemical Imaging: Dimens. Reduction Fiber-Optic Array Improvements & Appl. to Laser-Induced Breakdown Spectroscopy, 1999, V53, #7, pp. 751-759.

Nelson, M. et al. "Single-Shot Multiwavelength Imageing of Laser Plumes," Applied Spectroscopy, 1998, V. 52, No. 2, pp. 179-187.

* cited by examiner

Structured Illumination / Collection

F.

E.

G.

H.

SYSTEM AND METHOD FOR FIBER ARRAY SPECTRAL TRANSLATOR BASED POLYMORPH SCREENING

PRIORITY INFORMATION

The instant disclosure claims the filing-date benefit of Provisional Application No. 60/778,794 filed 3 Mar. 2006, entitled "FAST (Fiber Array Spectral Translator) Based System and Method of Polymorph Screening", the disclosure of which is incorporated herein in its entirety. The instant disclosure is also related to pending U.S. patent application Ser. No. 10/812,233, filed 29 Mar. 2004, entitled "Method for Identifying Components of a Mixture via Spectral Analysis" and to pending U.S. patent application Ser. No. 11/000,683, filed 20 Nov. 2004, entitled "Multipoint Method for identifying Hazardous Agents", the disclosure of each is hereby incorporated by reference in its entirety. All of the foregoing are commonly assigned to the assignee of the instant disclosure.

BACKGROUND

A fiber array spectral translator ("FAST") system when used in conjunction with a photon detector allows massively parallel acquisition of full-spectral images. A FAST system can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional array on one end and a one dimensional (i.e., linear) array on the other end. The linear array is useful for interfacing with a photon detector, such as a charge-coupled device ("CCD"). The two-dimensional array end of the FAST is typically positioned to receive photons from a sample. The photons from the sample may be, for example, emitted by the sample, reflected off of the sample, refracted by the sample, fluoresce from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrograph of a photon detector, such as a charge-coupled device so as to apply the photons received at the two-dimensional end of the FAST to the detector rows of the photon detector.

One advantage of this type of apparatus over other spectroscopic apparatus is speed of analysis. A complete spectroscopic imaging data set can be acquired in the amount of time it takes to generate a single spectrum from a given material. Additionally, the FAST can be implemented with multiple detectors. The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end input into the photon detector.

Given the advantageous ability of a FAST system to acquire hundreds to thousands of full spectral range, spatially-resolved spectra, such as Raman spectra, substantially simultaneously, a FAST system may be used in a variety of situations to help resolve difficult spectrographic problems such as the presence of polymorphs of a compound, sometimes referred to as spectral unmixing.

Chemical images may generally be acquired using one of two classes of approaches: (1) scanning, and (2) widefield chemical imaging. In scanning methods, a radiation source is focused onto the surface of a sample and a spectrum from each spatial position is collected using a dispersive spectrograph or interferometer. Long data collection times are common with scanning methods since the duration of the experiment is proportional to the number of image pixels. Because of such long data collection times, scanned images are captured at low image definition, which relates directly to the limited utility of the technique as an imaging tool for the routine assessment of material morphology. Furthermore, the spatial resolution of the image is limited by the size of the source illumination on the sample and the rastering mechanism, which requires the use of moving mechanical parts that are challenging to operate reproducibly. In addition, for light-absorbing materials, scanning methods present an enormous challenge. These materials have low damage thresholds, requiring the use of low laser power densities to minimize local thermal expansion and sample degradation.

Despite the limitations, scanning methods are relatively mature techniques and have been applied in a number of applications. An advantage of scanning-based chemical imaging is the ability to capture the entire spectrum in an efficient manner. This advantage is best realized in the research evaluation of new material systems where the underlying spectroscopy is not well understood, and therefore, benefits may be available from the analysis of the entire spectrum.

In widefield chemical imaging, the entire sample field of view is illuminated and analyzed simultaneously. Numerous widefield chemical imaging approaches have been demonstrated, with the majority of methods involving the recording of an image at discrete spectral intervals though an imaging spectrometer (i.e., LCTF (Liquid Crystal Tunable Filter), AOTF (Acousto-Optic Tunable Filter), etc.).

Because both (X-Y) spatial dimensions are collected simultaneously in widefield Chemical Imaging using imaging spectrometers, the experiment duration is proportional to the number of spectral channels and not to the number of image pixels. The widefield advantages are best realized when high fidelity images at a limited number of wavelengths provide sufficient chemical and spatial information. In most materials characterization applications, only a limited number of spectral bands (typically<100) are required to analyze the analytes of interest. By reducing the number of spectral channels, the duration of the widefield experiment decreases without losing spatial resolution. In addition, time-dependent changes in the sample are only observed in the spectral dimension, which simplifies the flatfielding or analysis of chemical images in widefield imaging.

Conversely, attempts to reduce the duration of scanning experiments (in the scanning approach discussed above) compromise either the spatial resolution or the field of view. Reducing the number of spectral channels in scanning mode has little effect on the experiment duration since the entire chemical spectrum is captured simultaneously (in the scanning approach discussed above). Scanning experiments record time dependent sample changes as spatial variations. Pixels collected at different times often have induced spectral differences that complicate flatfield correction.

A phenomenon of Raman spectroscopy of crystalline materials (e.g., polymorphs) is the effect the crystal orientation (with respect to incident and scattered light) has on the resultant spectrum. The crystal orientation-dependent effects on the Raman spectra manifest themselves as changes in the relative band intensities and/or frequency positions. For a plurality of crystals that has a random orientation, the Raman spectrum of a single crystal can potentially be much different than a spectrum of the bulk material. This phenomenon can result in a false conclusion that the single crystal is a different polymorph than the reference material. This effect can be lessened by reducing the degree of polarization of the excitation illumination as well as minimizing the polarization dependence of the spectrometer.

Current Raman well-plate polymorph screening instruments typically involve the acquisition of Raman data in a semi-automated or fully-automated fashion. These instruments are typically configured in a point scanning format in which a laser beam is focused in a small spot in an attempt to localize the illumination and collection from a single crystal. Semi-automated scanning Raman analysis is typically first preceded with an optical (i.e., brightfield and/or polarized light microscopy) means of viewing the wells in the well-plate. A user then manually selects regions of interest followed by a subsequent automated Raman dispersive acquisition of those selected regions. This approach is susceptible to human subjectivity in targeting appropriate crystals for subsequent analysis. On the other hand, in a fully-automated configuration, a single or multipoint acquisition is performed in a blind fashion within each well of the well-plate. The acquisition time of the experiment in each case is proportional to the number of measurements acquired per well.

For most spectral unmixing methods to be effective, a minimum of 6-12 spectra must be acquired having some spectral variability representative of the compositional variance within the sample. To support this quantity of measurements using traditional Raman screening methods would result in extremely long experimental acquisition times since data is normally collected in a serial fashion.

The present disclosure provides methods and systems for overcoming the above-mentioned limitations of the prior art. In certain embodiments, the present disclosure describes a system and a methodology that each combine Raman spectroscopy performed in a manner that utilizes widefield illumination, simultaneous multipoint Raman spectral acquisition, and spectral unmixing for the purpose, for example, of high throughput polymorph screening. The use of FAST enables full spectral acquisition for hundreds to thousands of spatially resolved spectra in a single image frame—dramatically increasing data acquisition rates compared to current tunable filter based technologies. Software, hardware, and/or a combination of software and hardware may be used to extract the spatial/spectral information to reconstruct hyperspectral (chemical imaging) data cubes of the original object and/or determine the presence and/or quantities (actual or relative) of polymorphs present in a sample. Furthermore, FAST is a rugged technology that operates over an extensive spectral range from ultraviolet (UV) to infrared (IR).

Accordingly, it is on object of the present disclosure to provide a method for polymorph screening, comprising illuminating a sample using widefield illumination to thereby produce scattered photons, which may be Raman scattered photons; receiving the scattered photons substantially simultaneously from a plurality of spatial locations of the sample using a fiber array spectral translator and directing the scattered photons to a photon detector, where each fiber of the fiber array spectral translator may receive photons from a different region of the sample; detecting the scattered photons and providing therefrom plural spectra of the sample, which may be Raman spectra; and applying a spectral unmixing algorithm to the plural spectra to thereby determine the presence of one or more polymorphs in the sample.

It is another object of the present disclosure to provide a system for polymorph screening, comprising a photon source for illuminating a sample using widefield illumination to thereby produce scattered photons, which may be Raman scattered photons; a fiber array spectral translator for receiving the scattered photons substantially simultaneously from a plurality of spatial locations of the sample and directing the scattered photons to a photon detector, where each fiber of the fiber array spectral translator may receive photons from a different region of the sample; the photon detector for detecting the scattered photons and providing therefrom plural spectra of the sample, which may be Raman spectra; and a-microprocessor unit for applying a spectral unmixing algorithm to the plural spectra to thereby determine the presence of one or more polymorphs in the sample.

It is a further object of the present disclosure to provide a method for polymorph screening, comprising: illuminating a mixture with first photons in a widefield illumination manner to thereby produce second photons, such as Raman scattered photons, wherein the sample comprises a polymorph of a compound wherein first ones of the polymorph are disposed in a first orientation and second ones of the polymorph are disposed in a second orientation, and wherein first ones of the second photons are scattered from the first oriented polymorphs and second ones of the second photons are scattered from the second oriented polymorphs; receiving the second photons at a proximal end of a fiber array spectral translator comprising plural fibers wherein each fiber of the fiber array spectral translator is associated with a different predetermined region of the sample, where the regions may overlap; delivering the second photons at a distal end of the fiber array spectral translator to a photon detector; detecting the second photons and providing therefrom plural spectra, such as Raman spectra, comprising a first spectrum of the first oriented polymorphs and a second spectrum of the second oriented polymorphs; and applying a spectral unmixing algorithm to the plural spectra to thereby determine a quantity of the first and second oriented polymorphs.

It is yet a further object of the present disclosure to provide a system for polymorph screening, comprising a photon source for illuminating a mixture with first photons in a widefield illumination manner to thereby produce second photons, such as Raman scattered photons, wherein the sample comprises a polymorph of a compound wherein first ones of the polymorph are disposed in a first orientation and second ones of the polymorph are disposed in a second orientation, and wherein first ones of the second photons are scattered from the first oriented polymorphs and second ones of the second photons are scattered from the second oriented polymorphs; a fiber array spectral translator comprising plural fibers for receiving the second photons at a proximal end wherein each fiber of the fiber array spectral translator is associated with a different predetermined region of the sample, and for delivering the second photons at a distal end to a photon detector; the photon detector for detecting the second photons and providing therefrom plural spectra, such as Raman spectra, comprising a first spectrum of the first oriented polymorphs and a second spectrum of the second oriented polymorphs; and a microprocessor unit for applying a spectral unmixing algorithm to the plural spectra to thereby determine a quantity of the first and second oriented polymorphs.

It is still a further object of the present disclosure to provide a method for polymorph screening, comprising illuminating a sample with first photons in a widefield illumination manner to thereby produce second photons, such as Raman scattered photons, wherein the sample comprises a plurality of polymorphs of a compound wherein first ones of the second photons are scattered from a first polymorph and second ones of the second photons are scattered from a second polymorph; receiving the second photons at a proximal end of a fiber array spectral translator comprising plural fibers wherein each fiber of the fiber array spectral translator is associated with a different predetermined region of the sample; delivering the second photons at a distal end of the fiber array spectral translator to a photon detector; detecting the second photons and providing therefrom plural spectra, such as Raman spectra, comprising a first spectrum of the first polymorph and a second spectrum of the second polymorph; and applying a spectral unmixing algorithm to the plural spectra to thereby determine a quantity of each of the first and second polymorphs. Furthermore, first ones of the first polymorph may be disposed in a first orientation and second ones of the first polymorph may be disposed in a second orientation wherein a first subset of the first ones of the second photons are scattered from the first oriented polymorphs and a second subset of the first ones of the second photons are scattered from the second oriented polymorphs. Additionally, the first spectrum may comprise a third spectrum from the first oriented polymorphs and a fourth spectrum from the second oriented first polymorphs. Moreover, the spectral unmixing algorithm may also determine a quantity of the first oriented polymorphs and a quantity of the second oriented polymorphs.

It is another object of the present disclosure to provide a system for polymorph screening, comprising a photon source for illuminating a sample with first photons in a widefield illumination manner to thereby produce second photons, such as Raman scattered photons, wherein the sample comprises a plurality of polymorphs of a compound wherein first ones of the second photons are scattered from a first polymorph and second ones of the second photons are scattered from a second polymorph; a fiber array spectral translator comprising plural fibers for receiving the second photons at a proximal end wherein each fiber of the fiber array spectral translator is associated with a different predetermined region of the sample, and for delivering the second photons at a distal end to a photon detector; the photon detector for detecting the second photons and providing therefrom plural spectra, such as Raman spectra, comprising a first spectrum of the first polymorph and a second spectrum of the second polymorph; and a microprocessor unit for applying a spectral unmixing algorithm to the plural spectra to thereby determine a quantity of each of the first and second polymorphs. Furthermore, first ones of the first polymorph may be disposed in a first orientation and second ones of the first polymorph may be disposed in a second orientation wherein a first subset of the first ones of the second photons are scattered from the first oriented polymorphs and a second subset of the first ones of the second photons are scattered from the second oriented polymorphs. Additionally, the first spectrum may comprise a third spectrum from the first oriented polymorphs and a fourth spectrum from the second oriented polymorphs. Moreover, the microprocessor unit may apply the spectral unmixing algorithm to determine a quantity of the first oriented polymorphs and a quantity of the second oriented polymorphs.

DETAILED DESCRIPTION

Figure 1:
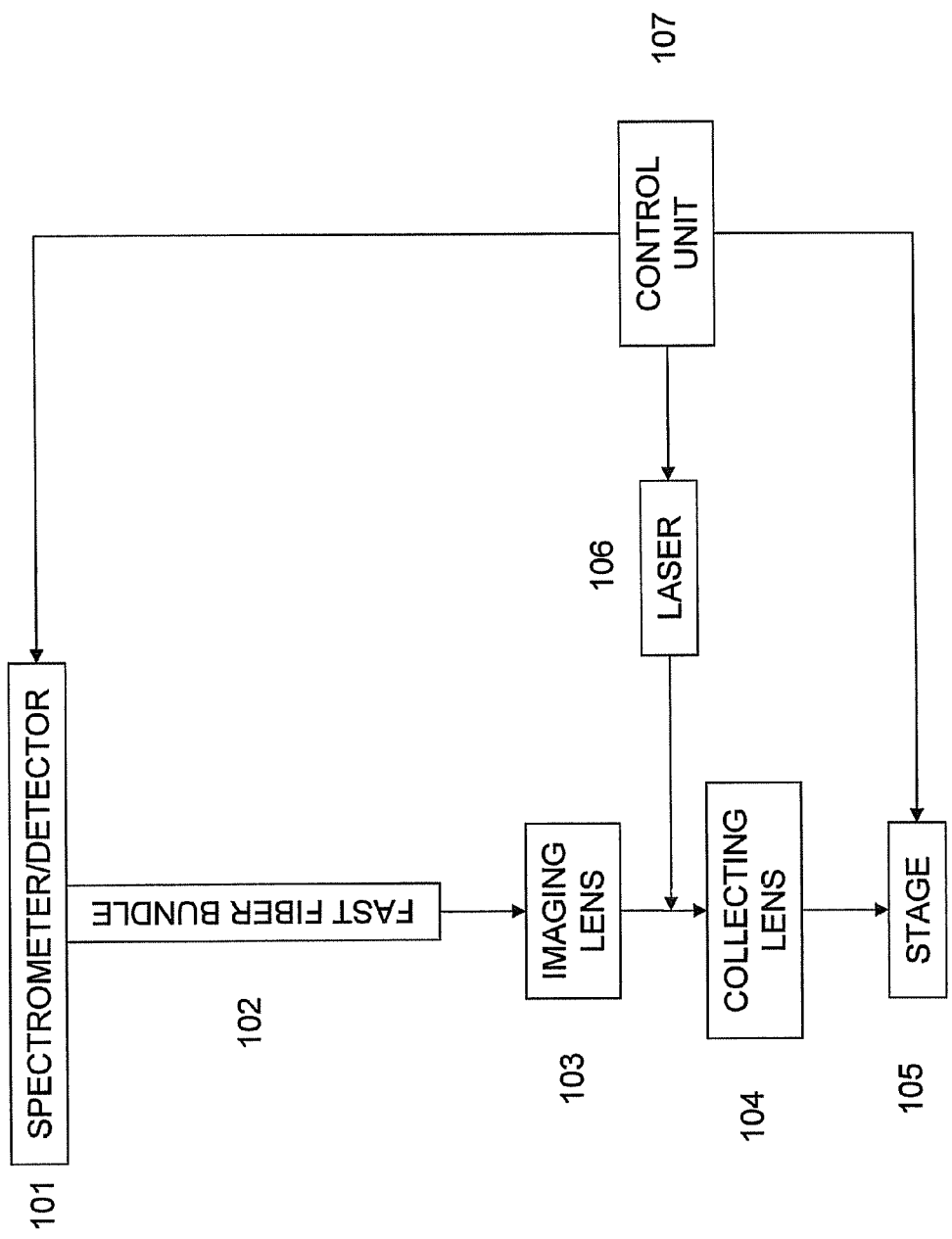
FIG. 1 is a schematic block diagram of a of a fiber array spectral translator ("FAST") based spectroscopy system.
Figure 2:
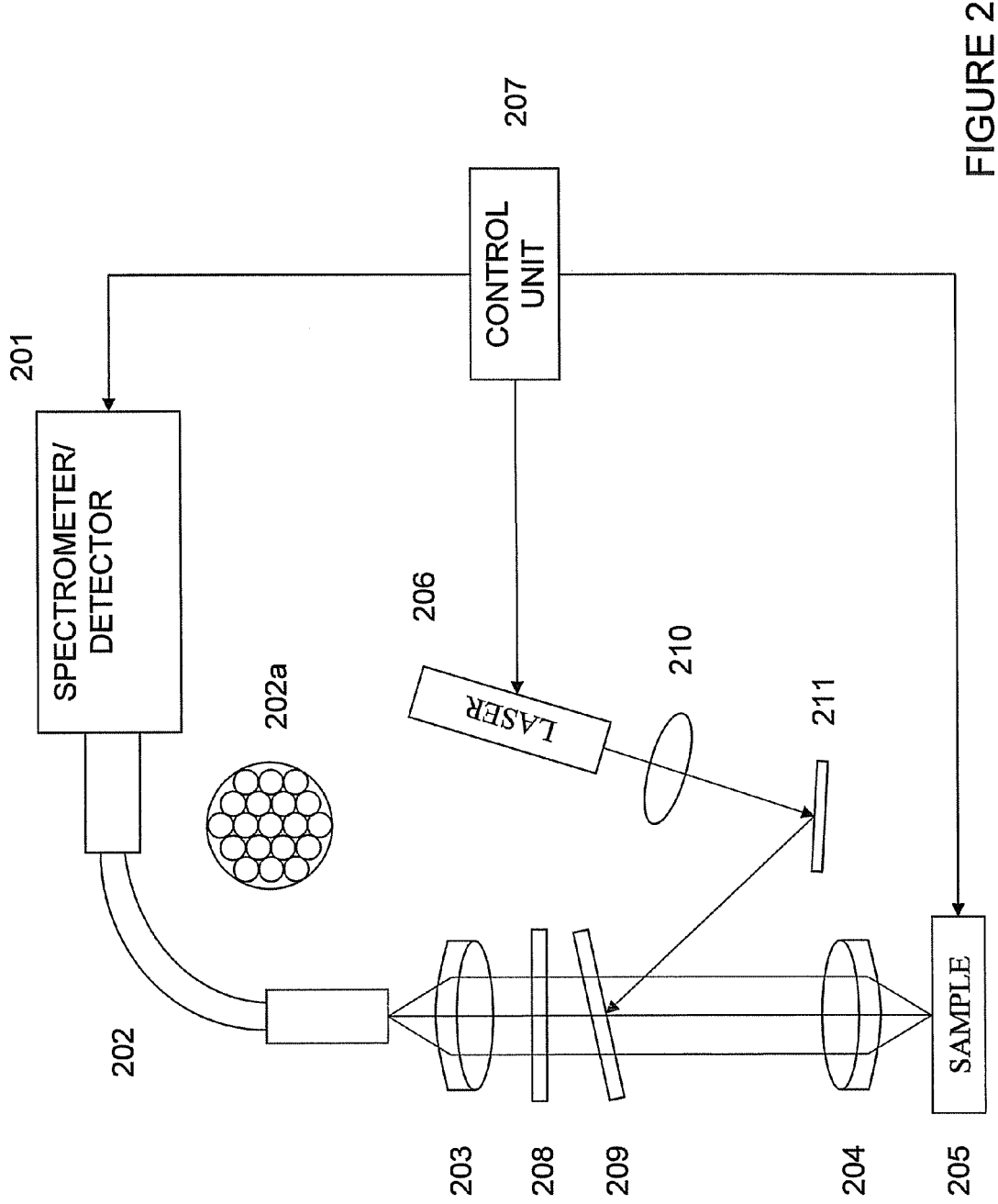
FIG. 2 is a is a schematic drawing of a FAST based spectroscopy system.
Figure 3:
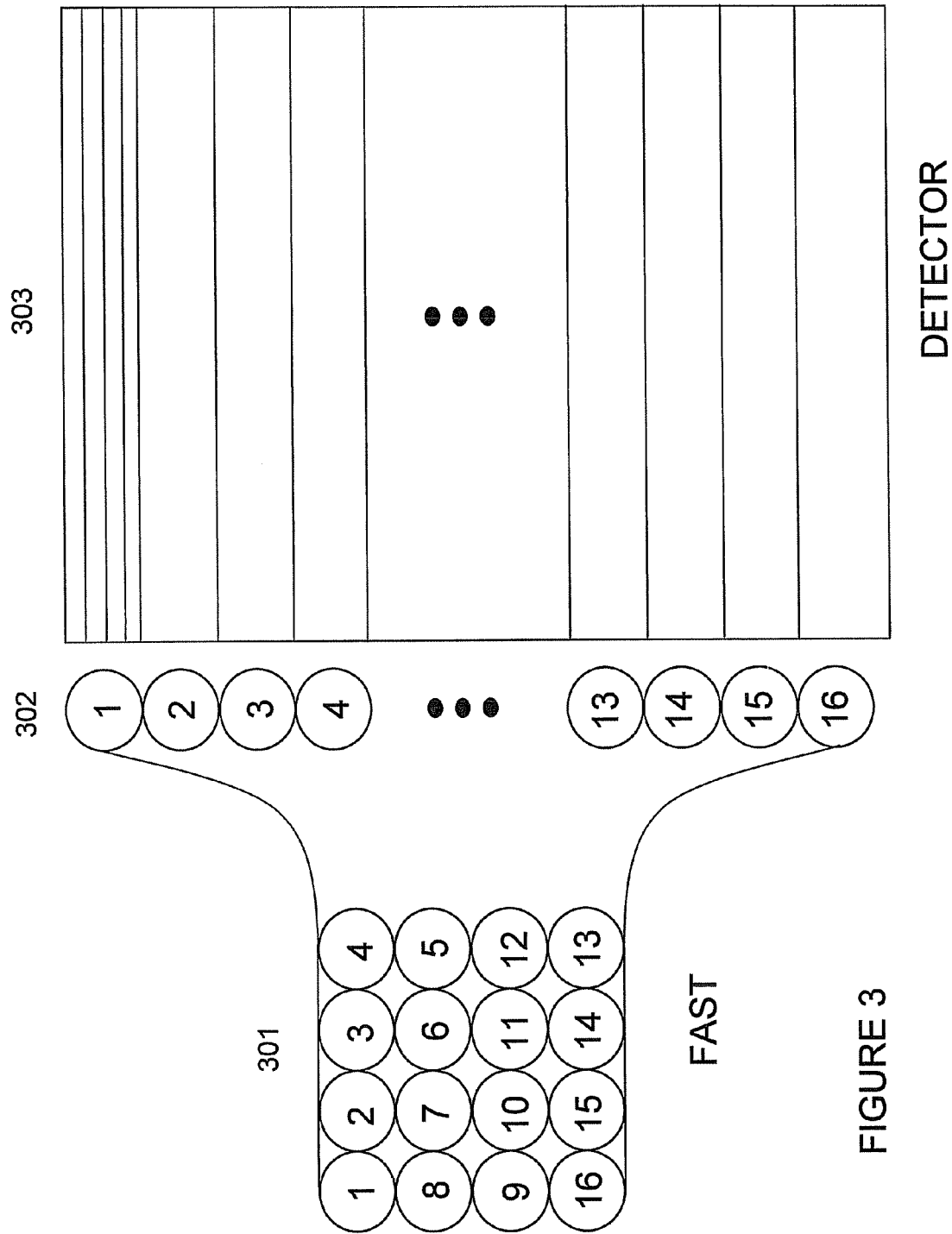
FIG. 3 is a schematic drawing of a FAST fiber layout showing an exemplary spatial mapping arrangement.

An emerging technology in the field of widefield chemical imaging is the use of fiber optic arrays. Briefly, FIG. 1 illustrates a block diagram of an exemplary Fiber Array Spectral Translator ("FAST")-based spectroscopy system. FIG. 2, on the other hand, provides a more detailed architectural view of the FAST system illustrated in FIG. 1. A FAST system may also be referred to as Dimension Reduction Arrays. FIG. 3 illustrates a simplified, exemplary, arrangement of optical fibers in a FAST fiber bundle having a two-dimensional ("2D") imaging end and a one-dimensional ("1D") distal end for feeding photons into a photon detector.

With reference now directed toward the various figures, FIG. 1 illustrates a block diagram of an exemplary FAST-based spectroscopy system including a spectrometer 101, a FAST fiber bundle 102, an imaging lens 103, a collecting lens 104, a stage 105 for holding, e.g., a 96-well plate containing samples which may be a mixture containing polymorphs of a compound, a photon source 106, such as the laser shown, and a control unit 107 for controlling the spectrometer 101, the photon source 106 and the stage 105. FIG. 2, on the other hand, provides a more detailed architectural view of the FAST system illustrated in FIG. 1. In FIG. 2, the system may include a spectrometer 201, a FAST fiber bundle 202, which may be arranged in a substantially circular 19-fiber arrangement as shown in cross-sectional view 202a, a lens 203, which may be an imaging lens, a lens 204, which may be a collecting lens, sample 205 which may be mounted in a well of a well plate and positioned on a stage, such as the stage 105 described above with respect to FIG. 1, a photon source 206, which may be a laser as shown, a control unit 207, which may control the spectrometer 201, the laser 206, and the sample 205, a filter 208 which may be a 0° filter such as a laser rejection filter, a filter 209 which may be a 7° filter, such as a laser rejection filter, a lens 210, which may be a focusing lens, and a mirror 211. A FAST system may also be referred to as a Dimension Reduction Array since, in an embodiment, the imaging end may be a 2D array and the distal end may be a 1D array. FAST technology can acquire hundreds to thousands of full spectral range, spatially resolved spectra, such as Raman spectra, simultaneously. This may be accomplished by focusing an image onto a two dimensional array of optical fibers (at the end of the fiber bundle which is proximal to the sample to be viewed) such as the FAST fiber bundle 202 which may be drawn into a one dimensional distal array (at the end of the fiber bundle which feeds the optical signals into the spectrometer/spectrograph, i.e., where the FAST fiber bundle 202 enters the spectrometer 201) with serpentine (or curvilinear) ordering as illustrated in the exemplary embodiment in FIG. 3. The one dimensional fiber stack may be coupled to an imaging spectrograph 201. Software and/or hardware may then extract the spectral/spatial information that is embedded in a single CCD image frame.

Referring now to FIG. 3, the construction of the FAST array requires knowledge of the position of each fiber at both the imaging end and the distal end of the array as shown, for example, in the simplified diagram for FIG. 3 where a total of sixteen fibers are shown numbered in correspondence between the imaging (or proximal) end 301 and the distal end 302 of the fiber bundle. As shown in FIG. 3, a FAST fiber bundle may feed optical information from its 2D non-linear imaging end 301 (which can be in any non-linear configuration, e.g., circular, square, rectangular, etc., and may contain more than the 16 fibers shown in the exemplary embodiment in FIG. 3) to its 2D linear distal end 302, which feeds the optical information into associated detector rows 303. The distal end may be positioned at the input to a photon detector 303, which may include a spectrometer/spectrograph and a CCD, a complementary metal oxide semiconductor ("CMOS") detector, or a focal plane array sensor (such as InGaAs, InSb, metal oxide semiconductor controlled thyristor ("MCT"), etc.). Photons exiting the distal end fibers may be collected by the various detector rows. Each fiber collects light from a fixed position in the two-dimensional array (imaging end) and transmits this light onto a fixed position on the detector (through that fiber's distal end).

FIG. 3 shows a non-limiting exemplary spatial arrangement of fibers at the imaging end 301 and the distal end 302. Additionally, as shown in FIG. 3, each fiber may span more than one detector row in detector 303, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

Thus, in an exemplary FAST application, a fiber bundle may be physically organized in 2D (X-Y) at the signal input end so as to image the sample in two dimensions. On the output side, however, the fibers in the fiber bundle may be stacked in a linear or curvilinear array (1D) (principally X or Y direction only depending on the slit placement) and aligned with a slit in the grating-based spectrometer so as to facilitate extraction of spectral info. It is known that a spectrometer works on a liner (1D) input. This 1D output from the fiber bundle may be fed to the spectrometer gratings (or other similar dispersive elements) to separate signal wavelengths. Each wavelength-dispersed signal (1D) from the gratings may be sent to the CCD detector as shown in the extremely simplified view of FIG. 3. Each column of CCD pixels may represent one wavelength. There may be 5 CCD pixels (or rows) mapped to an image point (or fiber) at a particular wavelength, for example. Thus, in the case of 1024 pixels in a column, around 204-205 (1024 divided by 5) image points (or linear fiber array outputs) can be accommodated. A 1D-to-2D array mapping may then organize each column of CCD back to or close to the original 2D fiber bundle arrangement so as to obtain the 2D image of the sample for the specific wavelength (also known as a 3D spectral image).

The FAST-based chemical imaging method may provide a significant speed of analysis. Using FAST, since two spatial dimensions and one spectral dimension of data may be collected in a single imaging frame, a complete chemical imaging data set can often be acquired in approximately the amount of time it takes to generate a single spectrum from a given material (which may be several seconds or less) with a conventional non-FAST method. Fusion of FAST-generated chemical images and high-spatial resolution images generated using other modalities can provide significant insight into the morphology and chemistry of materials. Furthermore, a FAST system may provide significant instrumentation cost reduction, expanded free spectral range (UV-IR), and optional sensitivity to polarization. A limitation of FAST is that the number of pixels in the reconstructed image is limited by the number of rows in the spectrograph's CCD detector. The resulting single image acquisition is typically a low fidelity image. A higher fidelity FAST image can be obtained by producing a montage of FAST images from adjacent regions of interest on the sample.

FAST enables full spectral acquisition for hundreds to thousands of spatially resolved spectra in a single image frame—dramatically increasing data acquisition rates compared to current tunable filter based technologies. Software and/or hardware may be used to extract the spatial/spectral information to reconstruct hyperspectral (chemical imaging) data cubes of the original object. Furthermore, FAST is a rugged technology that operates over an extensive spectral range (from UV to IR).

In the FAST optical system embodiment of FIG. 2, a two-lens imaging configuration is shown, although the present disclosure is not limited to such a configuration, as would be obvious to those of skill in the art. The system in FIG. 2 may include a collecting lens 204, an imaging lens 203, and some optics (e.g., filters 208 and 209, described above) for laser illumination for spectroscopy, such as Raman spectroscopy. The collecting lens 204 may be a doublet for focusing the laser beam onto the sample and collecting photons from the sample, such as Raman radiations/Raman scattered photons from the sample. The collecting lens 204 may also collimate the imaging beams (e.g., the Raman photons) and project images in infinity. The imaging lens 203 may also be a doublet and may be selected in such a way that when it is used together with the collecting lens 204, images, e.g., of Raman radiations, will be formed at its final focal plane. Because the imaging beams between the collecting lens 204 and the imaging lens 203 are collimated, it may be easier to introduce one of more laser filters, such as filters 208 and/or 209, into the FAST optics as shown in FIG. 2.

Figure 10:
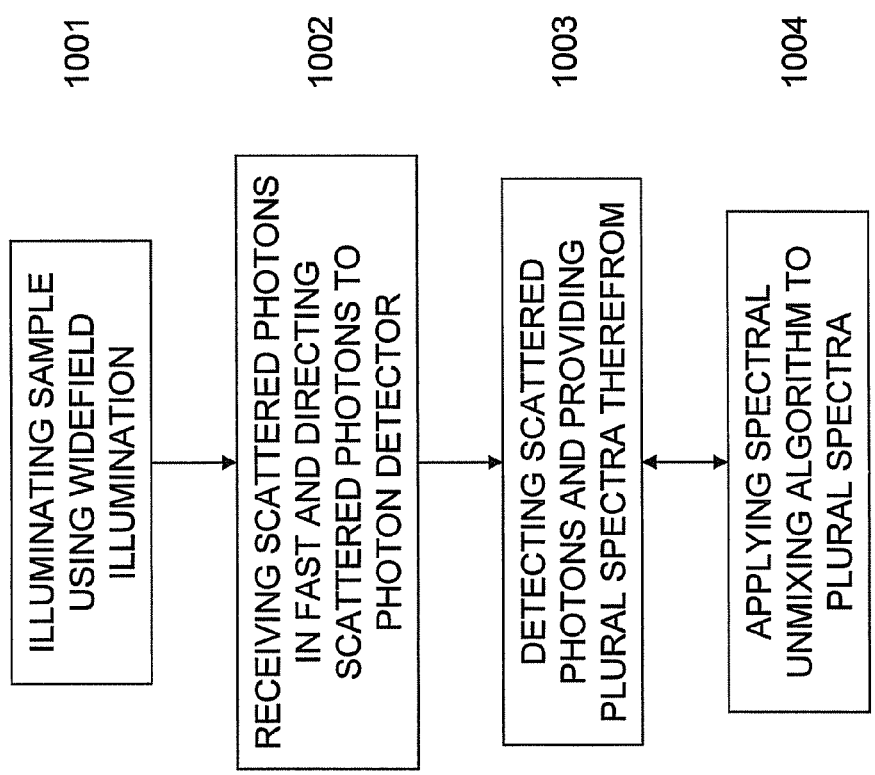
FIG. 10 is a flow chart of a method for polymorph screening using a FAST based spectroscopic system according to an embodiment of the disclosure.

In one embodiment of the present disclosure, the FAST system of FIG. 1 may be used to screen or detect polymorphs present in a sample (e.g., a 96-well plate, referred to above as stage 105 in FIG. 1). The detection may be accomplished by matching spectra of the observed target sample against a set of library spectra. Thus, in case of a mixture containing polymorphs, a spectrum of a polymorph crystal may be matched against a set of library spectra of various polymorphs to identify the polymorph or polymorphs present in the mixture. In one embodiment, the library spectra of a plurality of known polymorphs of a compound may be pre-stored electronically (e.g., in a computer memory used along with the FAST system of FIG. 1, as shown in FIG. 10 discussed below). Such spectra may have been obtained in a device-independent manner (i.e., the spectra may not be taken using the FAST system selected for current polymorph screening application). In an alternative embodiment, the library spectra may be generated using the same FAST system as that being used for current polymorph screening application at hand. Hence, in such an embodiment, the library spectra may be device-dependent and, hence, may be matched more accurately with the target polymorph spectra.

In one embodiment, there may be 19 fibers in the fiber bundle. As will be obvious to those of skill in the art, the present disclosure is not limited to a 19-fiber FAST bundle and can be implemented with any number of fibers in the FAST bundle in any type of 2D orientation at the proximal, or imaging, end. The fiber bundle may be sequentially focused on each well in the 96-well plate placed on the stage 105 of FIG. 1. The stage 105 may be designed to receive samples for spectroscopic analysis. Each well may contain a plurality of polymorphs, in which case the resulting spectrum may be a combination of individual polymorph spectra. Various spectral matching techniques may be employed to identify which known polymorphs are present in the well being investigated. Also, those spectra that do not match with the library spectra may indicate presence of unknown polymorphs in the sample at hand. Such information may be useful in further analyzing the sample for detection and identification of such new polymorphs.

Figures 4A, 4B, 4C, 4D, 4E:
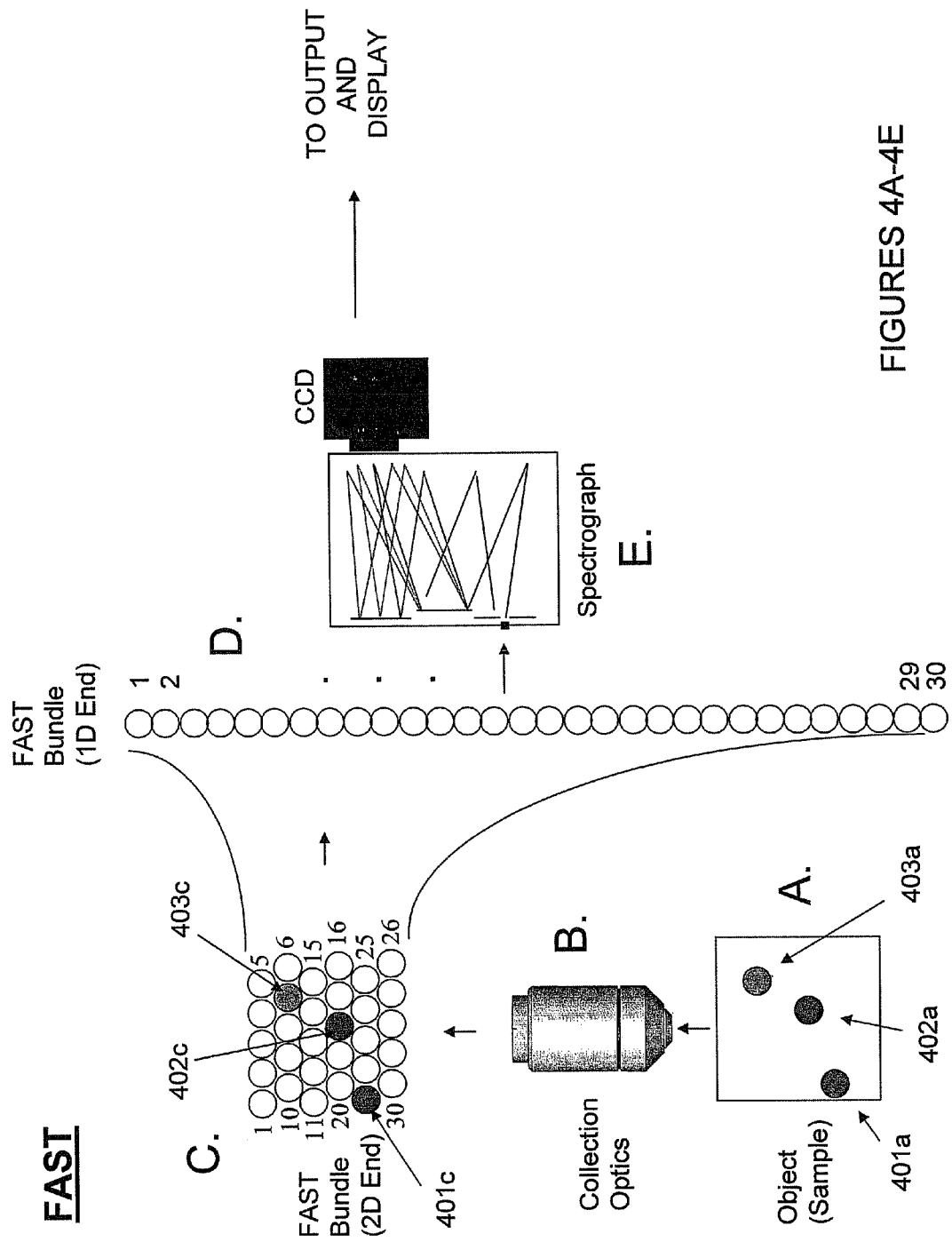
FIGS. 4A through 4H illustrate details of an exemplary FAST based spectroscopy system according to one embodiment of the disclosure.
Figures 4F, 4G, 4H:
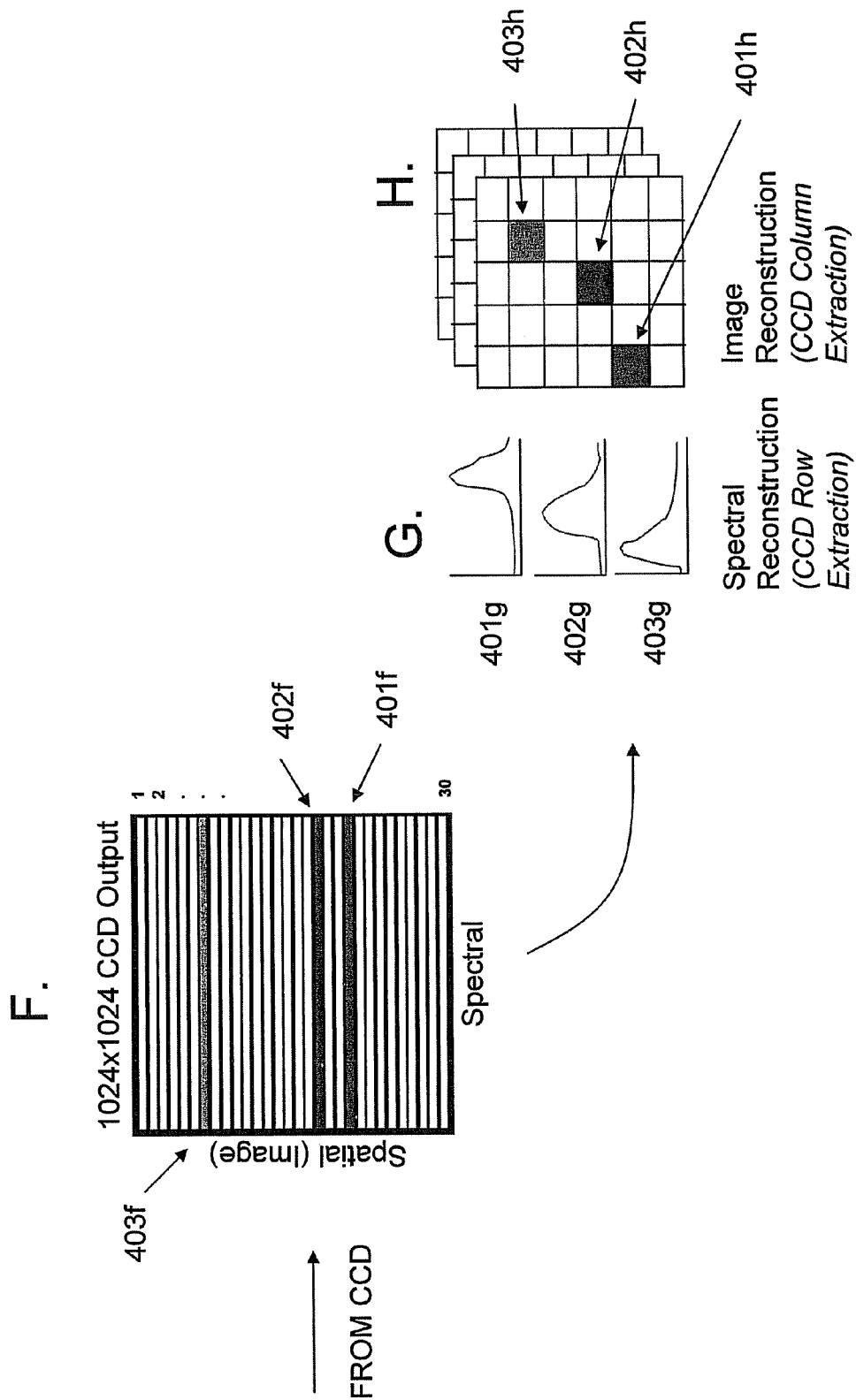

With reference now directed toward FIGS. 4A-4G, details of an exemplary FAST based spectroscopy system according to one embodiment of the disclosure are illustrated. As discussed above, FAST technology can acquire hundreds to thousands of full spectral range, spatially resolved Raman spectra simultaneously. This may be accomplished by focusing an image from a sample (FIG. 4A showing regions 401*a*, 402*a*, and 403*a*) using a light gathering optic (FIG. 4B) onto a two dimensional array of optical fibers (FIG. 4C showing regions 401*c*, 402*c*, and 403*c* which correspond to regions 401*a*, 402*a*, and 403*a*, respectively) such as a FAST bundle, that may be drawn into a one dimensional distal array with structured (i.e., serpentine or curvilinear) or unstructured (i.e., random) ordering (FIG. 4D). The one dimensional fiber stack may be coupled to a dispersive spectrograph (FIG. 4E) which may be connected to a detector, such as the CCD shown. Software, hardware, or a combination of the two may then extract the spectral/spatial information that is embedded in a single CCD image frame (FIG. 4F showing regions 401*f*, 402*f*, and 403*f* which correspond to regions 401*a*, 402*a*, and 403*a*, respectively) to produce spatial-specific spectra (FIG. 4G showing regions 401*g*, 402*g*, and 403*g* which correspond to regions 401*a*, 402*a*, and 403*a*, respectively) and/or spectral-specific images (FIG. 4H showing regions 401*h*, 402*h*, and 403*h* which correspond to regions 401*a*, 402*a*, and 403*a*, respectively) which may be displayed on an appropriate display device (e.g., a computer screen, a television, etc.). As shown in FIG. 4G, the spectral-specific spectra may be a CCD row extraction for spectral reconstruction. A 1D-to-2D array mapping may then organize each column of CCD information back to or close to the original 2D fiber bundle arrangement so as to obtain the 2D image of the sample for the specific wavelength (also known as a 3D spectral image and illustrated in FIG. 4H). As shown in FIG. 4H, the spatial-specific image may be a CCD column extraction for image reconstruction. Additionally, the display may include both a spectral reconstruction and an image reconstruction. Fiber array based chemical imaging has been demonstrated in several applications including Raman chemical imaging analysis of microcomposites and biomaterials and time-resolved atomic emission chemical imaging of laser-induced plumes.

FIGS. 5A through 5H show some exemplary uses of FAST for improved confocality for use in spectroscopic systems, such as for widefield chemical imaging. A sample shown schematically in FIG. 5A including regions 501*a*, 502*a*, and 503*a* may be illuminated globally (FIG. 5B), i.e., an entire area of the sample (or the entire sample) is illuminated, illuminated in a point-focused manner (FIG. 5C) where only one point or region of the sample is illuminated, in FIG. 5C region 502C is the only illuminated region of the sample, or randomly (FIG. 5D) where only the three regions 501*d*, 502*d*, 503*d* of the sample are illuminated. Regions 501'*x*', 502'*x*', and 503'*x*' throughout FIGS. 5A through 5H, where 'x' represents 'a' through 'h', are corresponding regions, respectively. Returning to FIG. 5C, the region 502*c* is the only illuminated region of the sample and this may be achieved numerous ways including structured fiber optic illumination using a FAST-based spectroscopic system with or without the use of optical lenses. In an embodiment, regions 501*a*, 502*a*, and 503*a* may represent three exemplary fibers in a fiber bundle of a FAST system (e.g., the FAST system of FIG. 1). It is observed here that the optical confocality of a measurement may be improved when combined with the use of FAST as discussed herein.

Figures 5A, 5B, 5C, 5D:
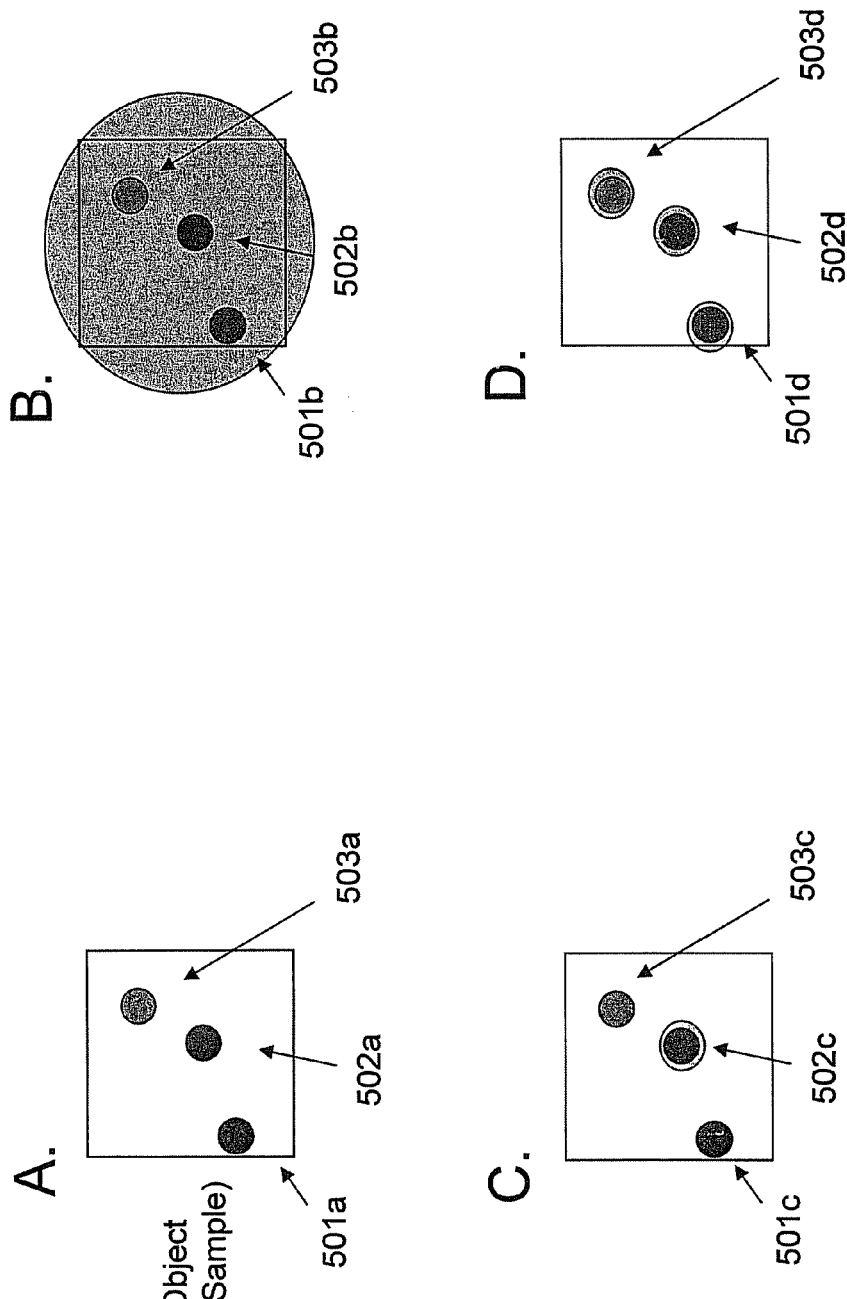
FIGS. 5A through 5D illustrate different structured illumination arrangements in a FAST based spectroscopy system according to embodiments of the disclosure.
Figure 5E:
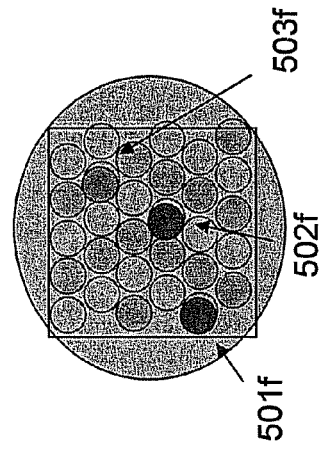
FIGS. 5E through 5H illustrate different structured illumination and collection arrangements in a FAST based spectroscopy system according to embodiments of the disclosure.
Figure 5F:
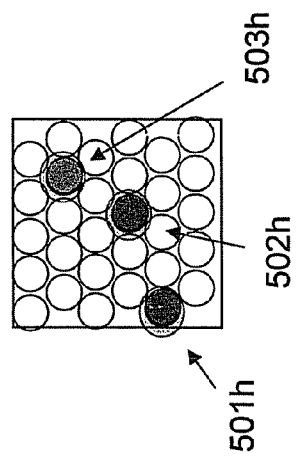
Figure 5G:
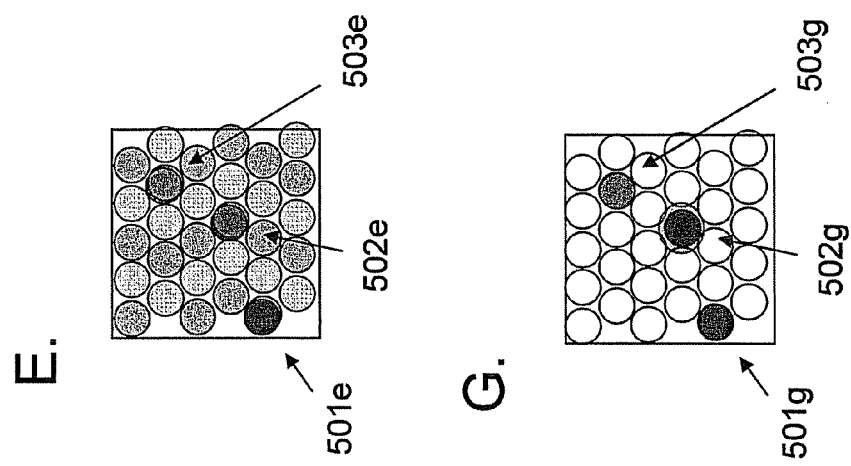
Figure 5H:
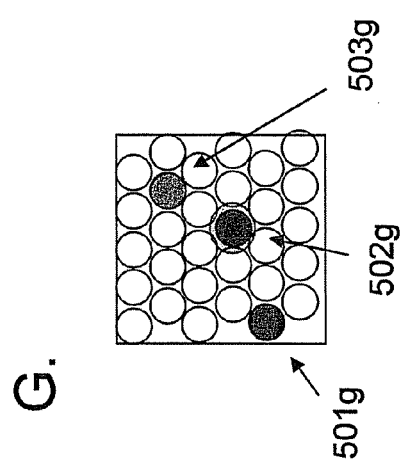

In FIG. 5E, the illumination of and collection of light from the sample is achieved through the same fiber. In other words, the illumination and collection optics is the same—the fibers in the single fiber bundle in the FAST system—in the embodiment of FIG. 5E. Specifically, FIG. 5E shows a 30 fiber FAST bundle, such as the one illustrated in FIG. 4C, where the illuminating light travels through each of the 30 fibers to illuminate the sample and each of the 30 fibers receives light from the sample and directs that received light to, for example, a photon detector. An embodiment of the disclosure contemplates, but the disclosure is not limited to, a situation where the illumination region and the collection region for any one fiber is mutually exclusive of the illumination region and the collection region of the other fibers in the FAST bundle. In the configuration shown schematically in FIG. 5F, the sample is globally illuminated (with an illumination source, e.g., an angled laser as shown in FIG. 2 or via a dispersive fiber) that is different from the light collection mechanism (i.e., one or more fibers in the fiber bundle of the FAST system) and light is gathered with all fibers within the FAST bundle. In FIG. 5G, the illumination is restricted to a small area around region 502*g* and the light is gathered from an individual fiber (e.g., the fiber represented by the circle 502*g* in FIG. 5G) or a smaller number of fibers consistent with the geometry and size of an object of interest in the sample. The illumination in FIG. 5G may be accomplished using a laser as shown, for example, in FIGS. 1 and 2, or using one or more fibers in the fiber bundle of the FAST (in which case the illumination source and the light collection source may be the same). In FIG. 5H, the illumination is structured and restricted to areas of interest (i.e., 501*h*, 502*h*, and 503*h*) within the sample while the collected radiation is primarily captured by a restricted number of fibers in the FAST bundle (corresponding to areas 501h, 502h, and 503h). In the embodiment of FIG. 5H, the structured illumination optics may include a laser coupled with an optical switch or a pattern creation optics to accomplish the desired structured illumination. The structured illumination can be accomplished either sequentially or simultaneously (i.e., in parallel). It is noted here that various illumination and collection approaches illustrated in FIGS. 5A through 5H may be part of a non-destructive imaging system of, for example, a chemical or biological sample.

Figure 6:
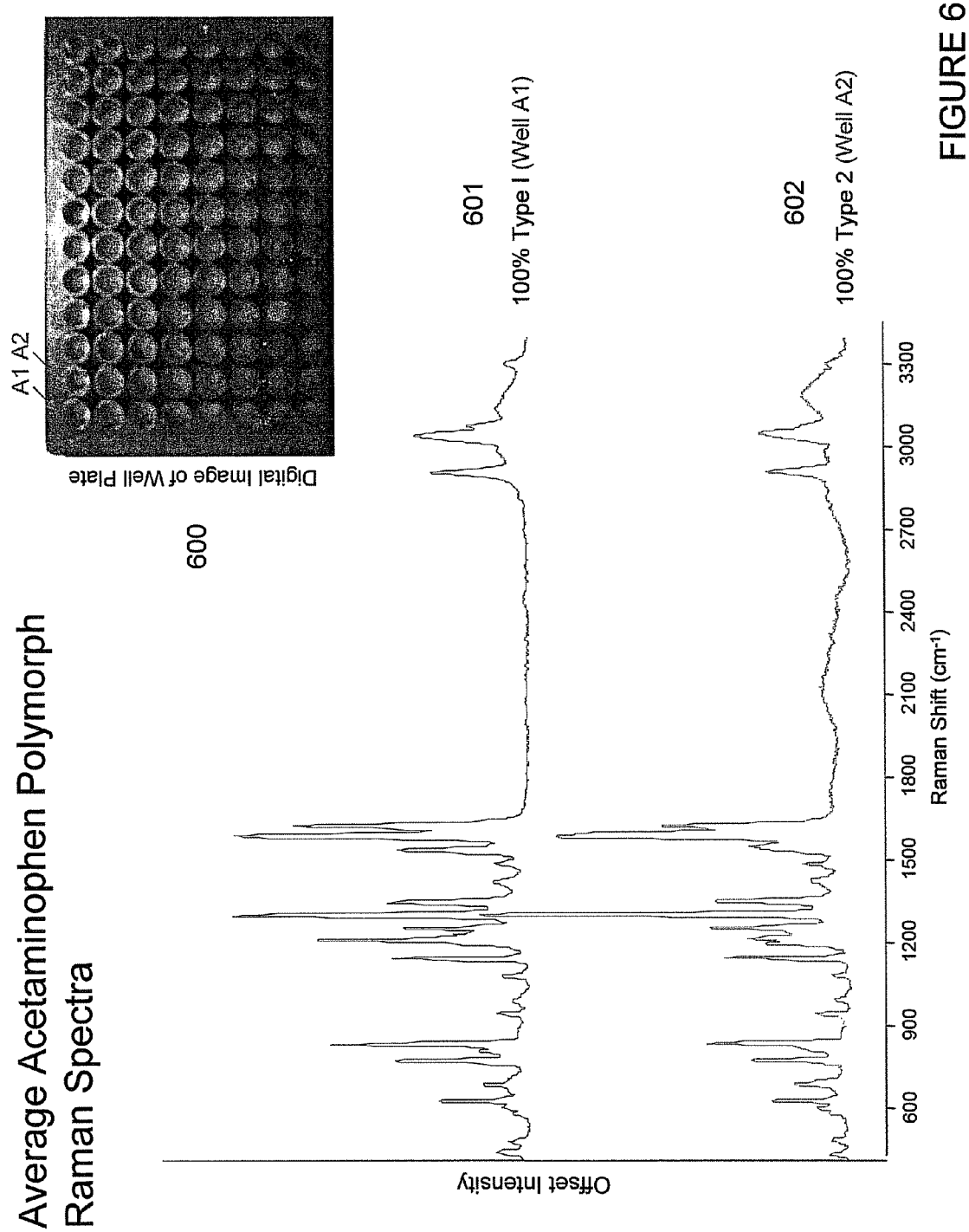
FIG. 6 illustrates a 96-well stage/test sample and a FAST-based average acetaminophen polymorph Raman spectra from each of two of the wells according to an embodiment of the disclosure.

Referring now to FIG. 6, item 600 illustrates a brightfield digital image of an exemplary 96-well plate along with two plots, 601 for well A1 and 602 for well A2, showing average Raman spectra (i.e., average spectra collected using all the light detected by the CCD detector from outputs of all fibers in a FAST bundle, as opposed to individual fiber spectra shown in FIG. 8, discussed below) of acetaminophen polymorphs taken from wells A1 and A2 in the well-plate 600 using a FAST system, such as the FAST system depicted by the block diagram of FIG. 1. The detection, screening, or identification of polymorph(s) present in a well may be accomplished by matching spectra of the observed target against a set of library spectra. Thus, in the case of a mixture containing polymorphs, a spectrum of a polymorph crystal may be matched against a set of library spectra of various polymorphs to identify the polymorph(s) present in the mixture (as well as the percentage proportion of the polymorph(s)) and also to flag the presence of unknown compounds in the mixture. For example, in plot 601 of FIG. 6, it is detected that well A1 contains 100% of acetaminophen polymorph Type-I, whereas in plot 602, it is detected that well A2 is found to contain 100% of acetaminophen polymorph Type-II.

Figure 7:
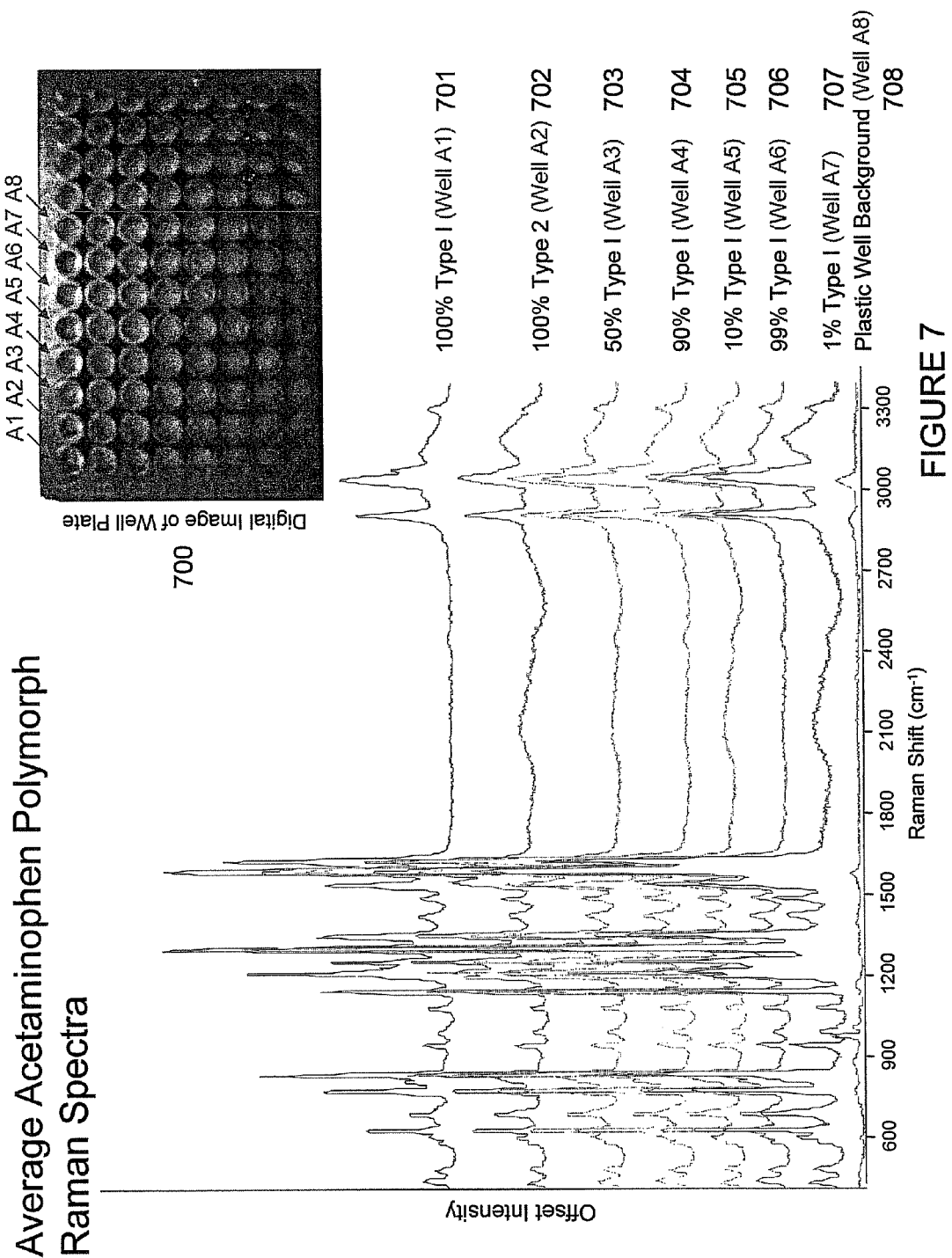
FIG. 7 illustrates a 96-well stage/test sample and a FAST-based average acetaminophen polymorph Raman spectra from each of eight of the wells according to an embodiment of the disclosure.

Referring now to FIG. 7, a brightfield digital image of an exemplary 96-well plate 700 is shown. The plots 701 through 708 illustrate average Raman spectra from eight wells (wells marked A1 through A8 in image 700) are shown. It is seen from plots 701 through 707 that each of the wells A1 through A7, respectively, is detected to contain some percentage of acetaminophen Type-I or Type-II polymorphs. Spectrum 708 from well A8 provides the spectrum of the plastic background of the well-plate. It is seen that each well A1 through A7 may contain a different proportion of polymorphs. For example, from plot 703, well A3 is identified to contain only 50% of acetaminophen Type-1 polymorph, whereas from plot 704, well A4 is found to have 90% of the same polymorph.

Figure 8:
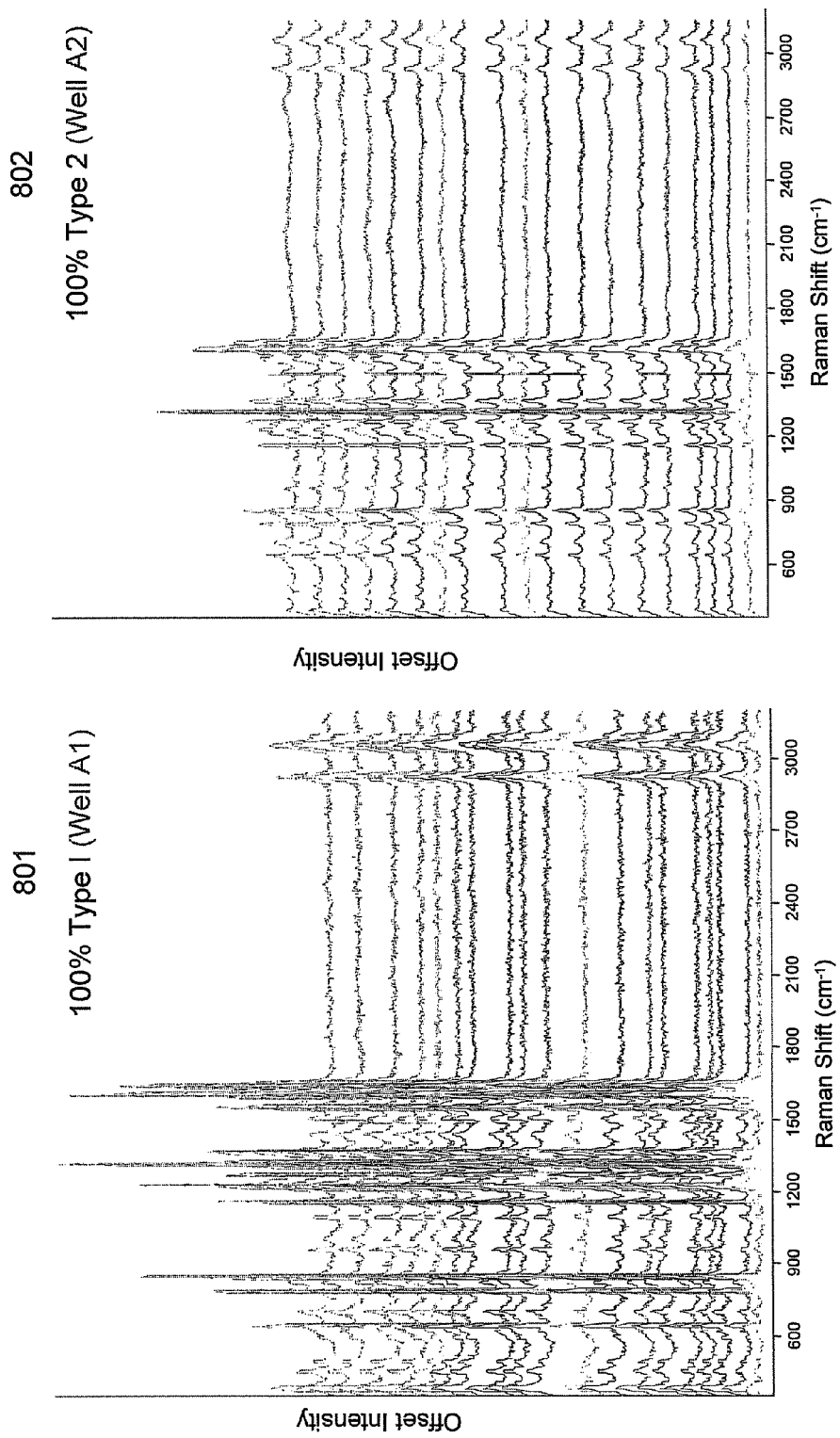
FIG. 8 illustrates a FAST-based acetaminophen polymorph Raman spectra from individual fibers of the FAST bundle for each of two of the wells according to an embodiment of the disclosure.

Turning now to FIG. 8, in each of plots 801 and 802 there is depicted spectrum from individual fiber for each of the 19 fibers in the FAST fiber bundle according to one embodiment of the present disclosure. The plots 801 and 802 are for wells A1 and A2, respectively, identified in FIG. 6. As mentioned above, all of the 19 fibers (or however many fibers there may be in the FAST bundle) may be used to screen polymorph(s) present in a well. Like the plots 601 and 602 of FIG. 6, the plots 801 and 802 of FIG. 8 relate to two of the 96 wells, wells A1 and A2 only. However, the plots 801 and 802 of FIG. 8 illustrate individual fiber spectra (for each of the 19 fibers in this embodiment) for each of wells A1 and A2, where well A1 contains 100% polymorph Type 1 and well A2 contains 100% polymorph Type 2 of acetaminophen, instead of the resulting or average spectra of all fiber outputs shown in plots 601 and 602, respectively, in FIG. 6.

In one embodiment, the present disclosure describes a methodology that combines Raman spectroscopy performed in a manner that utilizes widefield illumination, simultaneous multipoint Raman spectral acquisition, and spectral unmixing for the purpose of high throughput polymorph screening. Features of this methodology include: (a) high throughput polymorph screening to reduce crystal orientation effects on Raman spectra; (b) in-well multi-polymorph screening using increased statistical sampling; and (c) multipoint spectral sampling to enable spectral unmixing.

Embodiments of the present disclosure may utilize widefield illumination to reduce the effect of sensitivity to crystal orientation. A phenomenon of spectroscopy, specifically Raman spectroscopy, of crystalline materials (e.g., polymorphs) is the effect that the crystal orientation (with respect to incident and scattered light) has on the resultant spectrum. While the following discussion involves Raman spectroscopy, those of skill in the art will understand that the discussion may also apply to other types of spectroscopy. The crystal orientation-dependent effects on the Raman spectra manifest themselves as changes in the relative band intensities and/or frequency positions. For a plurality of crystals that has a random orientation, the Raman spectrum of a single crystal can potentially be much different than a spectrum of the bulk material. This phenomenon can result in a false conclusion that the single crystal is a different polymorph than the reference material. This effect can be lessened by reducing the degree of polarization of the excitation illumination as well as minimizing the polarization dependence of the spectrometer. Alternatively, according to one embodiment of the present disclosure, the field-of-view or sampling of a plurality of crystals simultaneously can reduce the polarization dependency. A consequence of the latter is the potential of having a resultant spectrum that is representative of the mixture of components. Algorithms embodied in software, hardware, or a combination of software and hardware utilizing one or more spectral unmixing approaches may be then used to qualify and quantify the individual component spectra.

In one embodiment of the present disclosure, Raman scattered radiation is intentionally collected from a plurality of crystals (instead of a single crystal) to minimize crystal orientation dependence. Thereafter, simultaneous multipoint detection may be used to support spectral unmixing algorithms to improve upon sampling statistics, enhance automation and reduce human error associated with state-of-the-art Raman polymorph screening equipment.

As mentioned above, FIG. 1 illustrates, in block diagram form, a system schematic of a FAST-based polymorph screening system according to one embodiment of the present disclosure. The system of FIG. 1 may be used to deliver widefield illumination to the sample, so as to minimize dependence of Raman spectra on orientation of various crystals. The widefield illumination may be accomplished using, for example, the structural arrangement of FIG. 2, where a laser beam is expanded with lens 210 and reflected with a laser rejection filter (e.g., the 7° filter 209) before passing through a focusing lens 204 onto target sample 205. Such widefield illumination is representatively illustrated as FIG. 5F by a circle of illumination surrounding the object (or sample) geometry, and a few exemplary fibers 501f, 502f, and 503f (from the fiber bundle in the FAST system of FIG. 1) shown with false-colored dots located within the sample geometry.

The foregoing describes a FAST-based system and method to accomplish high throughput polymorph screening while reducing crystal orientation effects on Raman spectra. Current methods typically require a manual selection of individual crystals prior to collection of a single Raman spectrum. In the prior art approach, special care must be taken to restrict spectral analysis to the single crystal, to orient the crystal properly (one skilled in the art may typically minimize crystal orientation effects by seeking out single crystals in a particular orientation for subsequent analysis), and to use equipment that has reduced sensitivity to polarization (e.g., an instrument with lower optical throughput). On the other hand, in the present disclosure, the FAST-based method according to one embodiment of the present disclosure is a rapid, high-throughput method that is semi- to fully-automatable.

Embodiments of the present disclosure may also utilize in-well multi-polymorph screening with increased statistical sampling and reduced experiment times. Current Raman well-plate polymorph screening instruments typically involve the acquisition of Raman data in a semi-automated or fully-automated fashion. These instruments are typically configured in a point scanning format in which a laser beam is focused in a small spot in an attempt to localize the illumination and collection from a single crystal. Semi-automated scanning Raman analysis is typically first preceded with an optical (i.e., brightfield and/or polarized light microscopy) means of viewing the wells in the well-plate. A user then manually selects regions of interest followed by a subsequent automated Raman dispersive acquisition of those selected regions. This approach is susceptible to human subjectivity in targeting appropriate crystals for subsequent analysis. On the other hand, in a fully-automated configuration, a single or multipoint acquisition is performed in a blind fashion within each well of the well-plate. The acquisition time of the experiment in each case is proportional to the number of measurements acquired per well.

In one embodiment of the present disclosure, the FAST fiber bundle in the system of FIG. 1 may be utilized to automatically collect multiple Raman spectra within a given well of the well-plate (e.g., a 96-well plate). The multiple spectra are collected simultaneously (by using a plurality of fibers in the FAST fiber bundle in parallel) enabling the experimental time to be proportional to the number of wells to be characterized instead of being proportional to the number of measurements acquired per well as is the case in the traditional state-of-the-art approaches. Further, such FAST-based methodology allows improved sampling statistics because of the simultaneous multipoint acquisition of Raman data. The FAST-based blind or automatic acquisition eliminates the human subjectivity of targeting. This FAST-based in-well screening method enables a more comprehensive analysis of all of the polymorph forms that may be present in the well.

The in-well polymorph screening discussed in the preceding paragraph may be implemented using the FAST configuration of FIGS. 1-2. With respect to the FAST system of FIG. 2, it is observed that Raman scattered radiation may be collected/collimated through focusing lens 204 and filtered through laser rejection filters (filters 208 and 209, which may be 0° and 7° filters). Lens 203 then focuses the collected and filtered Raman scattered radiation onto a proximal, close-packed, 19-fiber (for example) FAST collection bundle that is drawn into a linear array of fiber optics at a distal end as discussed hereinbefore. Those of skill in the art will readily understand that the present disclosure is not limited to a 19-fiber FAST bundle. The linear array may then be inserted into the entrance slit of a dispersive spectrograph equipped with a 1024×256 TE cooled CCD detector as illustrated by the spectrometer/detector 201 in FIG. 2, or the spectrograph and CCD in FIG. 4E, or the spectrometer/photon detector 904 in FIG. 9. Each fiber in the FAST bundle transmits light that can be mapped to spatially independent locations (i.e., multipoint) in the sample. The relatively large number of measurements (using a plurality of fibers over a single well) improves the statistical sampling involved in the measurement and reduces the human subjectivity associated with crystal targeting.

Figure 9:
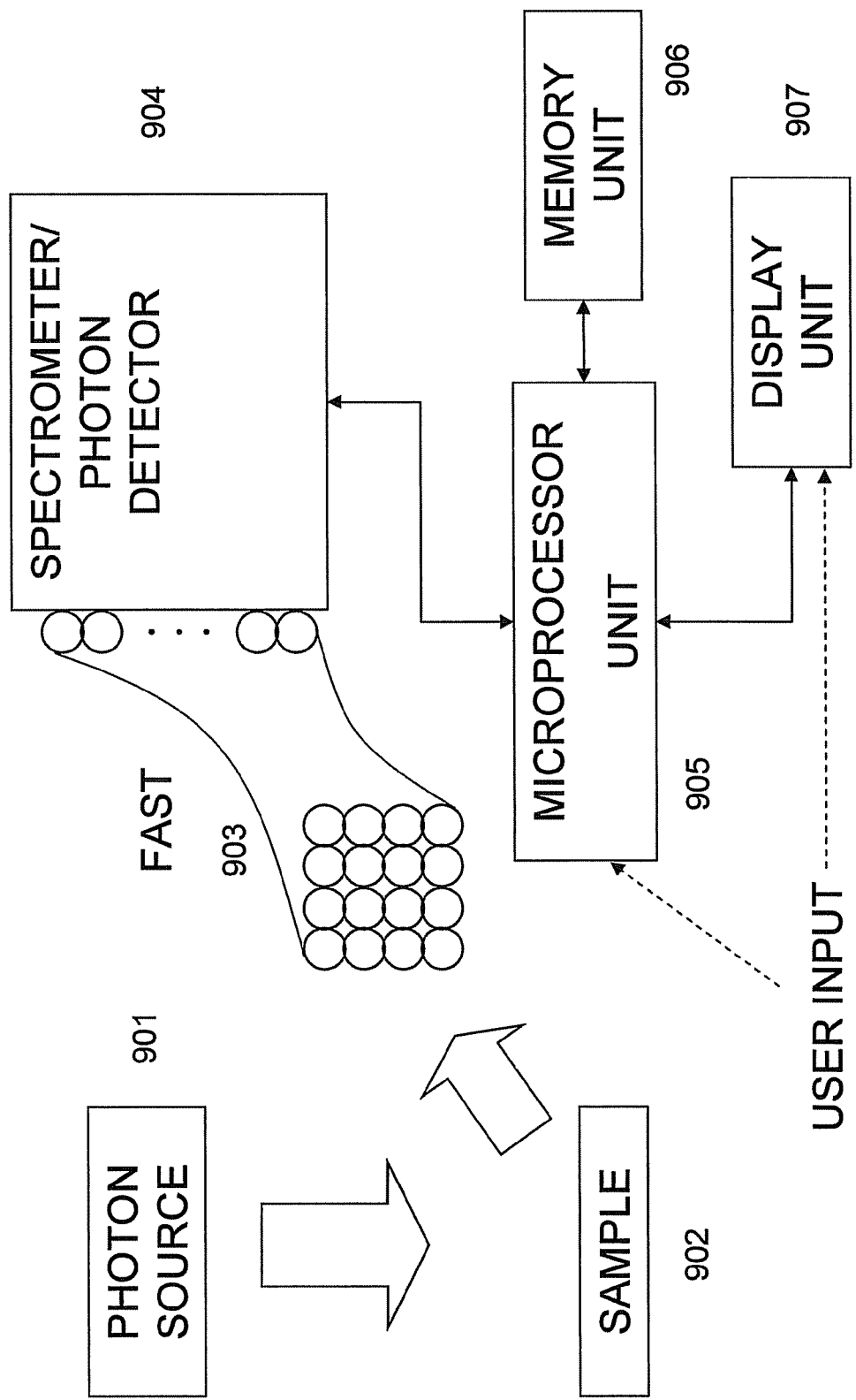
FIG. 9 is a block diagram of a FAST based spectroscopic system with optional user input according to one embodiment of the disclosure.

Embodiments of the present disclosure may also utilize multipoint spectral sampling to enable spectral unmixing. For most spectral unmixing methods to be effective, a minimum of 6-12 spectra must usually be acquired having some spectral variability representative of the compositional variance within the sample. To support this quantity of measurements using traditional Raman screening methods would result in extremely long experimental acquisition times since data is normally collected in a serial fashion. A method according to one embodiment of the present disclosure provides a means to support the data quantity requirements for spectral unmixing algorithms in a highly efficient manner. Specifically, the FAST fiber bundle (e.g., as shown in FIGS. 1, 2, and 9) may provide a multipoint means (i.e., a plurality of fibers in the FAST fiber bundle may provide spectral sampling at multiple spatial locations) to collect tens to hundreds of spatially independent Raman spectra in a parallel fashion. Once the plurality of spatially independent spectra are obtained, one or more spectral unmixing algorithms may be used to provide a determination of what compounds are present and what the relative abundances (sometimes referred to herein as "quantity") of each are in the sample region under analysis. The ChemImage Xpert™ software from ChemImage Corporation of Pittsburgh, Pa., has two tools available for performing the resolution of pure components spectra from a mixture—namely the Spectral Mixture Resolution tool and the Multivariate Curve Resolution tool.

The Spectral Mixture Resolution ("SMR") tool may use a set of reference spectra (spectra of known polymorphs or other crystalline structures) and find the best linear combination of reference spectra for each spectrum (pixel) in a given image or set of spectra (i.e., spatially independent spectra supplied by FAST). The function outputs a concentration image with one frame for each spectrum in the reference set, and a residual image. The concentration values for a given frame can vary between 0 and 1, and the set of concentration values for a given pixel (over all frames) sum to 1. A least squares fit may be used with the stipulation that no concentrations can be negative. Two images may be displayed: (1) a residual image, and (2) a concentration map. The residual image may contain the spectral information not explained by the library spectra. If the imaged sample contains only the substances represented by the reference spectra, an average spectrum of the residual image should represent only noise and have very small intensities compared to an average spectrum of the original image. If there are chemical species present in the sample that are not represented by the set of reference spectra, the residual image should contain spectra that represent the mixture of chemical species remaining after the set of reference spectra has been subtracted. In the context of mixture resolution for polymorph screening, the SMR residual provides a means for detecting the presence of unknown polymorphs. The second image is the concentration map that essentially maps the distribution of reference spectral species in the image. One concentration map may be generated for each reference spectrum.

The Multivariate Curve Resolution ("MCR") tool may first decompose the data matrix (i.e., spatially independent spectra supplied by FAST) into principal component ("PC") loadings (spectra) and scores (concentrations). Then, the MCR tool may use, for example, the alternating least squares ("ALS") technique to rotate the initial estimate of pure component spectra with non-negativity constraints. The concentration is estimated by projecting the data matrix onto the initial estimate of pure component spectra. Non-negativity constraints are applied to the estimated concentrations (negative concentrations are set to zero), which are then projected onto the data matrix to estimate the spectra. The newly estimated spectra are subjected to the non-negativity constraints (negative intensities are set to zero) and then used for estimating the new concentrations. This cycle of estimation of concentrations and spectra is repeated alternately until convergence is achieved or one of the termination criteria is met.

MCR requires an initial estimate of pure component spectra called a Key Set. One can provide an initial estimate in two ways. The most widely used method is Factor Analysis. A second method is to import an external spectral file representative of known pure component spectra. In the context of the present disclosure, the external spectral file may consist of spectra of known polymorphs.

Thus, the multipoint spectral sampling approach discussed hereinabove may provide improved sampling statistics both in data collection (with the use of FAST fibers for parallel, multipoint sampling) and data processing (with the use of the SMR or MCR tools discussed above).

The foregoing discloses Raman spectroscopy of polymorphs (or other crystalline structures) performed using a FAST-based system that utilizes widefield illumination, simultaneous multipoint Raman spectral acquisition, and in-well multipolymorph screening to accomplish high throughput polymorph detection and screening.

With reference now directed towards FIG. 9, an exemplary system according to an embodiment of the present disclosure is illustrated in block diagram form. A photon source 901 may illuminate with first photons a sample 902, which may contain polymorphs of a compound, to thereby produce second photons. The photon source 901 may be any typical photon source used for spectrographic purposes, such as a laser, white light source, UV (ultraviolet) lamp, etc. A fiber array spectral translator 903, having plural fibers receives the second photons and directs them to a spectrometer/photon detector 904 which is operatively connected to the fiber array spectral translator. The spectrometer/photon detector 904 may include a dispersive spectrograph (not shown) or other similar equipment as is known in the art. The spectrometer/photon detector 904 detects the second photons to thereby obtain a first spectrum. A microprocessor unit 905 is operatively connected to the spectrometer/photon detector 904 and to a memory unit 906. The memory unit 906 may store a set of second spectra where each spectrum of the set of second spectra may be representative of a different polymorph of the compound (sample 902). The microprocessor unit 905 may compare the first spectrum with the set of second spectra to thereby determine the presence of one or more polymorphs in the mixture based on said comparison. A display unit 907 may be operatively connected to the microprocessor unit 905 for displaying spectra and/or images generated from the photons detected by the spectrometer/photon detector 904. Optionally, the microprocessor 905 and/or the display unit 907 may be adapted to accept user input, such as via a computer mouse or pointing device, a keyboard, or, in the case of the display unit 907, a touch-screen. The user input, as described above, may include user selection of specific information for display of specific spectra and/or images.

FIG. 10 is a flow chart of a method for polymorph screening according to an embodiment of the disclosure. At block 1001, a sample is illuminated using widefield illumination, which may be accomplished with a laser. At block 1002 photons scattered from the sample are received by fibers in a FAST bundle and the photons are directed towards a photon detector. At block 1003, the photons are detected and plural spectra are provided from the photons. At block 1004, a spectral unmixing algorithm is applied to the plural spectra to thereby determine the presence, or quantity (i.e., relative abundance) of one or more polymorphs in the sample. The scattered photons may be Raman scattered photons and the spectra may be Raman spectra. Additionally, the fibers in the FAST bundle may receive the scattered photons from different regions of the sample, although parts of neighboring regions may overlap one another. The spectral unmixing algorithm may be a Spectral Mixture Resolution algorithm, a Multivariate Curve Resolution algorithm, or another appropriate algorithm.

Figure 11:
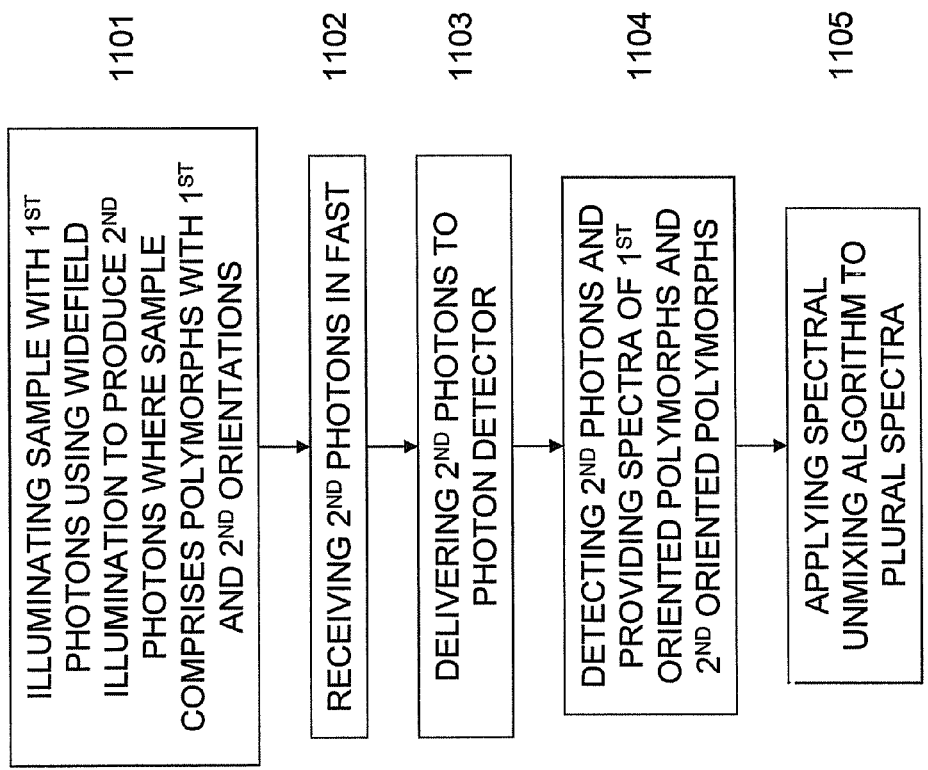
FIG. 11 is a flow chart of a method for polymorph screening using a FAST based spectroscopic system according to an embodiment of the disclosure.

FIG. 11 is a flow chart of a method for polymorph screening according to an embodiment of the disclosure. At block 1101, a sample is illuminated with first photons using a widefield illumination procedure to thereby produce second photons. The sample may comprise polymorphs of a first orientation and polymorphs of a second orientation, such that the second photons contain photons scattered by the first-oriented polymorphs and the second-oriented polymorphs. At block 1102, the second photons are received in a FAST bundle. At block 1103, the second photons received by the FAST bundle are delivered to a photon detector. At block 1104, the second photons are detected and spectra based on the second photons are provided. The spectra may include a first spectrum derived from photons scattered by the first-oriented polymorphs and a second spectrum derived from photons scattered by the second-oriented polymorphs. At block 1105, a spectral unmixing algorithm may be applied to the plural spectra and/or to the first and/or second spectra individually. The second photons may be Raman scattered photons and the spectra may be Raman spectra. Additionally, the fibers in the FAST bundle may receive the scattered photons from different regions of the sample, although parts of neighboring regions may overlap one another. The spectral unmixing algorithm may be a Spectral Mixture Resolution algorithm, a Multivariate Curve Resolution algorithm, or another appropriate algorithm.

Figure 12:
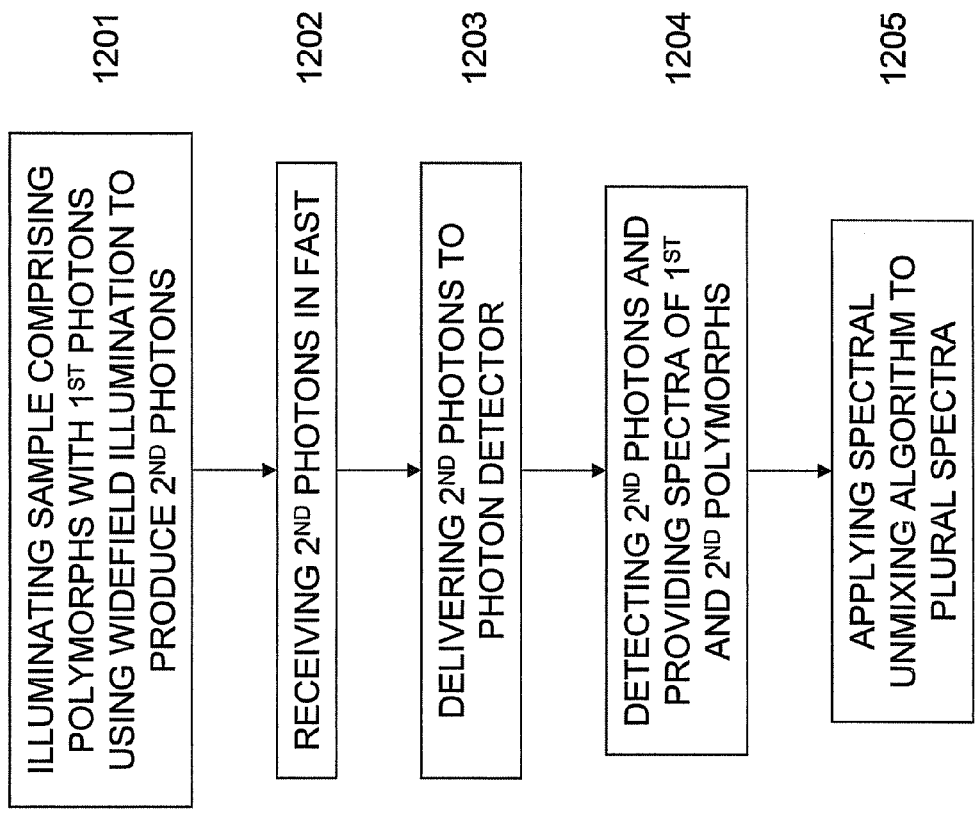
FIG. 12 is a flow chart of a method for polymorph screening using a FAST based spectroscopic system according to an embodiment of the disclosure.

FIG. 12 is a method for polymorph screening according to an embodiment of the disclosure. At block 1201, a sample is illuminated with first photons using a widefield illumination procedure to thereby produce second photons. The sample may comprise polymorphs and the polymorphs may include polymorphs of a first orientation and polymorphs of a second orientation, such that the second photons contain photons scattered by the first-oriented polymorphs and the second-oriented polymorphs. At block 1202, the second photons are received in a FAST bundle. At block 1203, the second photons received by the FAST bundle are delivered to a photon detector. At block 1204, the second photons are detected and spectra based on the second photons are provided. The spectra may include a first spectrum from the first polymorphs and a second spectrum from the second polymorphs. Additionally, the first spectrum may include a third spectrum derived from photons scattered by the first-oriented polymorphs and the second spectrum may include a fourth spectrum derived from photons scattered by the second-oriented polymorphs. At block 1205, a spectral unmixing algorithm may be applied to the plural spectra and/or to the first and/or second spectra individually and/or to the third and/or fourth spectra individually. The second photons may be Raman scattered photons and the spectra may be Raman spectra. Additionally, the fibers in the FAST bundle may receive the scattered photons from different regions of the sample, although parts of neighboring regions may overlap one another. The spectral unmixing algorithm may be a Spectral Mixture Resolution algorithm, a Multivariate Curve Resolution algorithm, or another appropriate algorithm.

The above description is not intended and should not be construed to be limited to the examples given but should be granted the fill breadth of protection afforded by the appended claims and equivalents thereto. Although the disclosure is described using illustrative embodiments provided herein, it should be understood that the principles of the disclosure are not limited thereto and may include modification thereto and permutations thereof.

We claim:

1. A method for polymorph screening, comprising:
illuminating a sample using widefield illumination to thereby produce scattered photons;
receiving said scattered photons substantially simultaneously from a plurality of spatial locations of said sample using a fiber array spectral translator and directing said scattered photons to a photon detector;
detecting said scattered photons and providing therefrom plural spectra of said sample; and
applying a spectral unmixing algorithm to said plural spectra to thereby determine the presence of one or more polymorphs in said sample.

2. The method of claim 1 wherein said scattered photons are Raman scattered photons.

3. The method of claim 2 wherein said spectra are Raman spectra.

4. The method of claim 1 wherein said widefield illumination comprises illuminating said sample with a laser.

5. The method of claim 1 wherein each fiber of said fiber array spectral translator receives Raman scattered photons from a different region of said sample.

6. The method of claim 5 wherein ones of said different regions overlap.

7. The method of claim 1 wherein said photon detector is selected from the group consisting of: charge-coupled device ("CCD"), complementary metal oxide semiconductor ("CMOS") detector, and focal plane array sensor.

8. The method of claim 1 wherein said spectral unmixing algorithm is a Spectral Mixture Resolution algorithm.

9. The method of claim 1 wherein said spectral unmixing algorithm is a Multivariate Curve Resolution algorithm.

10. The method of claim 1 wherein said sample is disposed in a well of a well plate.

11. A system for polymorph screening, comprising:
a photon source for illuminating a sample using widefield illumination to thereby produce scattered photons;
a fiber array spectral translator for receiving said scattered photons substantially simultaneously from a plurality of spatial locations of said sample and directing said scattered photons to a photon detector;
said photon detector for detecting said scattered photons and providing therefrom plural spectra of said sample; and
a microprocessor unit for applying a spectral unmixing algorithm to said plural spectra to thereby determine the presence of one or more polymorphs in said sample.

12. The system of claim 11 wherein said scattered photons are Raman scattered photons.

13. The system of claim 12 wherein said spectra are Raman spectra.

14. The system of claim 11 wherein said photon source comprises a laser.

15. The system of claim 11 wherein each fiber of said fiber array spectral translator receives Raman scattered photons from a different region of said sample.

16. The system of claim 15 wherein ones of said different regions overlap.

17. The system of claim 11 wherein said photon detector is selected from the group consisting of: charge-coupled device ("CCD"), complementary metal oxide semiconductor ("CMOS") detector, and focal plane array sensor.

18. The system of claim 11 wherein said spectral unmixing algorithm is a Spectral Mixture Resolution algorithm.

19. The system of claim 11 wherein said spectral unmixing algorithm is a Multivariate Curve Resolution algorithm.

20. The system of claim 11 wherein said sample is disposed in a well of a well plate.

21. The system of claim 11 wherein said microprocessor unit runs a software program for applying said spectral unmixing algorithm.

22. A method for polymorph screening, comprising:
illuminating a sample with first photons in a widefield illumination manner to thereby produce second photons, wherein said sample comprises a polymorph of a compound wherein first ones of said polymorph are disposed in a first orientation and second ones of said polymorph are disposed in a second orientation, and wherein first ones of said second photons are scattered from said first oriented polymorphs and second ones of said second photons are scattered from said second oriented polymorphs;
receiving said second photons at a proximal end of a fiber array spectral translator comprising plural fibers wherein each fiber of said fiber array spectral translator is associated with a different predetermined region of said sample;
delivering said second photons at a distal end of said fiber array spectral translator to a photon detector;
detecting said second photons and providing therefrom plural spectra comprising a first spectrum of said first oriented polymorphs and a second spectrum of said second oriented polymorphs; and
applying a spectral unmixing algorithm to said plural spectra to thereby determine a quantity of said first and second oriented polymorphs.

23. The method of claim 22 wherein said second photons are photons scattered by said sample.

24. The method of claim 23 wherein said scattered photons are Raman scattered photons.

25. The method of claim 24 wherein said plural spectra are Raman spectra.

26. The method of claim 22 wherein said widefield illumination comprises illuminating said sample with a laser.

27. The method of claim 22 wherein each fiber of said fiber array spectral translator receives Raman scattered photons from a different region of said sample.

28. The method of claim 27 wherein ones of said different regions overlap.

29. The method of claim 22 wherein said photon detector is selected from the group consisting of: charge-coupled device ("CCD"), complementary metal oxide semiconductor ("CMOS") detector, and focal plane array sensor.

30. The method of claim 22 wherein said spectral unmixing algorithm is a Spectral Mixture Resolution algorithm.

31. The method of claim 22 wherein said spectral unmixing algorithm is a Multivariate Curve Resolution algorithm.

32. The method of claim 22 wherein said sample is disposed in a well of a well plate.

33. A system for polymorph screening, comprising:
a photon source for illuminating a sample with first photons in a widefield illumination manner to thereby produce second photons, wherein said sample comprises a polymorph of a compound wherein first ones of said polymorph are disposed in a first orientation and second ones of said polymorph are disposed in a second orientation, and wherein first ones of said second photons are scattered from said first oriented polymorphs and second ones of said second photons are scattered from said second oriented polymorphs;

a fiber array spectral translator comprising plural fibers for receiving said second photons at a proximal end wherein each fiber of said fiber array spectral translator is associated with a different predetermined region of said sample, and for delivering said second photons at a distal end to a photon detector;

said photon detector for detecting said second photons and providing therefrom plural spectra comprising a first spectrum of said first oriented polymorphs and a second spectrum of said second oriented polymorphs; and a microprocessor unit for applying a spectral unmixing algorithm to said plural spectra to thereby determine a quantity of said first and second oriented polymorphs.

34. The system of claim 33 wherein said second photons are photons scattered by said sample.

35. The system of claim 34 wherein said scattered photons are Raman scattered photons.

36. The system of claim 35 wherein said plural spectra are Raman spectra.

37. The system of claim 33 wherein said widefield illumination comprises illuminating said sample with a laser.

38. The system of claim 33 wherein each fiber of said fiber array spectral translator receives Raman scattered photons from a different region of said sample.

39. The system of claim 38 wherein ones of said different regions overlap.

40. The system of claim 33 wherein said photon detector is selected from the group consisting of: charge-coupled device ("CCD"), complementary metal oxide semiconductor ("CMOS") detector, and focal plane array sensor.

41. The system of claim 33 wherein said spectral unmixing algorithm is a Spectral Mixture Resolution algorithm.

42. The system of claim 33 wherein said spectral unmixing algorithm is a Multivariate Curve Resolution algorithm.

43. The system of claim 33 wherein said sample is disposed in a well of a well plate.

44. The system of claim 33 wherein said microprocessor unit runs a software program for applying said spectral unmixing algorithm.

45. A method for polymorph screening, comprising:
illuminating a sample with first photons in a widefield illumination manner to thereby produce second photons, wherein said sample comprises a plurality of polymorphs of a compound wherein first ones of said second photons are scattered from a first polymorph and second ones of said second photons are scattered from a second polymorph;
receiving said second photons at a proximal end of a fiber array spectral translator comprising plural fibers wherein each fiber of said fiber array spectral translator is associated with a different predetermined region of said sample;
delivering said second photons at a distal end of said fiber array spectral translator to a photon detector;
detecting said second photons and providing therefrom plural spectra comprising a first spectrum of said first polymorph and a second spectrum of said second polymorph; and
applying a spectral unmixing algorithm to said plural spectra to thereby determine a quantity of each of said first and second polymorphs.

46. The method of claim 45 wherein said second photons are photons scattered by said sample.

47. The method of claim 46 wherein said scattered photons are Raman scattered photons.

48. The method of claim 47 wherein said plural spectra are Raman spectra.

49. The method of claim 45 wherein said widefield illumination comprises illuminating said sample with a laser.

50. The method of claim 45 wherein each fiber of said fiber array spectral translator receives Raman scattered photons from a different region of said sample.

51. The method of claim 50 wherein ones of said different regions overlap.

52. The method of claim 45 wherein said photon detector is selected from the group consisting of: charge-coupled device ("CCD"), complementary metal oxide semiconductor ("CMOS") detector, and focal plane array sensor.

53. The method of claim 45 wherein said spectral unmixing algorithm is a Spectral Mixture Resolution algorithm.

54. The method of claim 45 wherein said spectral unmixing algorithm is a Multivariate Curve Resolution algorithm.

55. The method of claim 45 wherein first ones of said first polymorph are disposed in a first orientation and second ones of said first polymorph are disposed in a second orientation.

56. The method of claim 55 wherein a first subset of said first ones of said second photons are scattered from said first oriented polymorphs and a second subset of said first ones of said second photons are scattered from said second oriented polymorphs.

57. The method of claim 56 wherein said first spectrum comprises a third spectrum from said first oriented polymorphs and a fourth spectrum from said second oriented first polymorphs.

58. The method of claim 57 wherein applying said spectral unmixing algorithm includes determining a quantity of said first oriented polymorphs and a quantity of said second oriented polymorphs.

59. A system for polymorph screening, comprising:
a photon source for illuminating a sample with first photons in a widefield illumination manner to thereby produce second photons, wherein said sample comprises a plurality of polymorphs of a compound wherein first ones of said second photons are scattered from a first polymorph and second ones of said second photons are scattered from a second polymorph;
a fiber array spectral translator comprising plural fibers for receiving said second photons at a proximal end wherein each fiber of said fiber array spectral translator is associated with a different predetermined region of said sample, and for delivering said second photons at a distal end to a photon detector;
said photon detector for detecting said second photons and providing therefrom plural spectra comprising a first spectrum of said first polymorph and a second spectrum of said second polymorph; and
a microprocessor unit for applying a spectral unmixing algorithm to said plural spectra to thereby determine a quantity of each of said first and second polymorphs.

60. The system of claim 59 wherein said second photons are photons scattered by said sample.

61. The system of claim 60 wherein said scattered photons are Raman scattered photons.

62. The system of claim 61 wherein said plural spectra are Raman spectra.

63. The system of claim 59 wherein said widefield illumination comprises illuminating said sample with a laser.

64. The system of claim 59 wherein each fiber of said fiber array spectral translator receives Raman scattered photons from a different region of said sample.

65. The system of claim 64 wherein ones of said different regions overlap.

66. The system of claim 59 wherein said photon detector is selected from the group consisting of: charge-coupled device ("CCD"), complementary metal oxide semiconductor ("CMOS") detector, and focal plane array sensor.

67. The system of claim 59 wherein said spectral unmixing algorithm is a Spectral Mixture Resolution algorithm.

68. The system of claim 59 wherein said spectral unmixing algorithm is a Multivariate Curve Resolution algorithm.

69. The system of claim 59 wherein said microprocessor unit runs a software program for applying said spectral unmixing algorithm.

70. The system of claim 59 wherein first ones of said first polymorph are disposed in a first orientation and second ones of said first polymorph are disposed in a second orientation.

71. The system of claim 70 wherein a first subset of said first ones of said second photons are scattered from said first oriented polymorphs and a second subset of said first ones of said second photons are scattered from said second oriented polymorphs.

72. The system of claim 71 wherein said first spectrum comprises a third spectrum from said first oriented polymorphs and a fourth spectrum from said second oriented polymorphs.

73. The system of claim 72 wherein said microprocessor unit applies said spectral unmixing algorithm to determine a quantity of said first oriented polymorphs and a quantity of said second oriented polymorphs.

* * * * *